United States Patent
Kizilbash et al.

(10) Patent No.: US 11,801,209 B2
(45) Date of Patent: Oct. 31, 2023

(54) COOLING AND FLAVOR BOOSTING COMPOSITIONS

(71) Applicant: Firmenich SA, Meyrin (CH)

(72) Inventors: Muhammad A. Kizilbash, Plainsboro, NJ (US); Qingbo Ouyang, Shanghai (CN); Wenji Yuan, Shanghai (CN); Jan Thomas Haines, Singapore (SG)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/637,905

(22) PCT Filed: Dec. 12, 2018

(86) PCT No.: PCT/EP2018/084467
§ 371 (c)(1),
(2) Date: Feb. 10, 2020

(87) PCT Pub. No.: WO2019/121193
PCT Pub. Date: Jun. 27, 2019

(65) Prior Publication Data
US 2020/0306156 A1    Oct. 1, 2020

(30) Foreign Application Priority Data
Dec. 21, 2017   (WO) ............... PCT/CN2017/117692

(51) Int. Cl.
| | | |
|---|---|---|
| *A61K 8/37* | (2006.01) | |
| *A61K 8/92* | (2006.01) | |
| *A61K 8/34* | (2006.01) | |
| *A61K 8/49* | (2006.01) | |
| *A61K 8/35* | (2006.01) | |
| *A61K 8/365* | (2006.01) | |
| *A61Q 11/00* | (2006.01) | |

(52) U.S. Cl.
CPC ............... *A61K 8/37* (2013.01); *A61K 8/345* (2013.01); *A61K 8/35* (2013.01); *A61K 8/365* (2013.01); *A61K 8/498* (2013.01); *A61K 8/4946* (2013.01); *A61K 8/4973* (2013.01); *A61K 8/922* (2013.01); *A61Q 11/00* (2013.01); *A61K 2800/244* (2013.01)

(58) Field of Classification Search
CPC . A61K 8/37; A61K 8/345; A61K 8/35; A61K 8/365; A61K 8/4946; A61K 8/49734; A61K 8/498; A61K 8/922; A61K 2800/244; A61Q 11/00
See application file for complete search history.

(56) References Cited

U.S. PATENT DOCUMENTS

| | | | |
|---|---|---|---|
| 5,580,545 A | 12/1996 | Washino et al. | |
| 2009/0226549 A1* | 9/2009 | Hughes | A61K 36/235 424/734 |
| 2010/0233102 A1* | 9/2010 | Krammer | A23C 9/1544 424/54 |
| 2016/0376263 A1* | 12/2016 | Patron | C07D 413/14 514/784 |

FOREIGN PATENT DOCUMENTS

JP    2006104229 A    4/2006

OTHER PUBLICATIONS

Google search—Mar. 24, 2021 (Year: 2021).*
S. Alankar. A Review on Peppermint Oil. Asian Journal of Pharmaceutical and Clinical Research, vol. 2, Issue 2, Apr.-Jun. 2009, 27-33 (Year: 2009).*
Riffat Tahira, Muhammad Naeemullah, Fazal Akbar. Major Phenolic Acids of Local and Exotic Mint Germplasm Grown in Islamabad. Pak. J. Bot., 43: 151-154, Special Issue, Dec. 2011. (Year: 2011).*
Scifinder_search_1-18-22_CAS_1119831-25-2.pdf (Year: 2022).*
Methyl_acetate_flavoring_-_Google_Scholar_1-18-22.pdf (Year: 2022).*

* cited by examiner

*Primary Examiner* — Michael P Cohen

(57) ABSTRACT

The various aspects presented herein relate to the cooling and flavor boosting compositions, and their use thereof.

8 Claims, No Drawings

COOLING AND FLAVOR BOOSTING COMPOSITIONS

CROSS REFERENCE TO RELATED APPLICATIONS

The present application claims priority to International Patent Application Serial No. PCT/CN2017/117692, filed on Dec. 21, 2017, the entire contents of which is hereby incorporated by reference in its entirety.

FIELD OF THE INVENTION

The various aspects presented herein relate to the cooling and flavor boosting compositions, and their use thereof.

BACKGROUND

Oral care products such as dentifrice and mouthwash are used by consumers as part of their oral care hygiene regimens. Oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, or essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression which can be broadly characterized as mouth feel aesthetics. Calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of certain oral products containing ingredients that promote staining, such as cationic antimicrobials and metal salts.

Consequently, daily oral care at home requires products with multiple ingredients working by different mechanisms to provide the complete range of therapeutic and aesthetic benefits, including anticaries, antimicrobial, antigingivitis, antiplaque, anticalculus and anti-erosion, as well as antiodor, mouth refreshment, stain removal, stain control and tooth whitening. It is frequently necessary to combine actives and additives, many of which have the disadvantage of causing negative aesthetics during use, in particular unpleasant taste and sensations and stain promotion. The unpleasant taste and mouth sensations have been described as having one or more of bitter, metallic, astringent, salty, numbing, stinging, burning, prickling, and even irritating aspects. Typical ingredients for oral care use that are associated with these aesthetic negatives include antimicrobial agents such as cetyl pyridinium chloride, chlorhexidine, stannous and zinc salts; tooth bleaching agents such as peroxides; antitartar agents such as pyrophosphate, tripolyphosphate and hexametaphosphate; and excipients such as baking soda and surfactants.

To mitigate the aesthetic negatives from these ingredients, oral care products are typically formulated with flavoring agents, sweeteners and coolants to taste as good as possible and provide a pleasant experience. In particular, it is desirable for oral care products to provide a refreshing cooling sensation during and after use.

Accordingly, in some aspects, the present disclosure provides oral care compositions comprising a flavor system comprising cooling compounds combined with one or more compounds that potentiate the flavor, cooling and refreshing sensation provided by the cooling compound. In some aspect, the potentiation is the onset, intensity or impact and/or duration of the flavor, cooling and refreshing sensation.

SUMMARY

One aspect presented herein, provides a composition, comprising:
  a) at least one cooling compound;
  b) at least one potentiating agent selected from the group consisting of: methyl acetate, (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, a mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[3,2-g]chromen-7-one, at least one polymethoxy flavonoid, 3-(1-((3,5-dimethylisoxazol-4-yl)methyl)-1H-pyrazol-4-yl)-1-(3-hydroxybenzyl)imidazolidine-2,4-dione, and combinations thereof;
    wherein the at least one potentiating agent is present in the composition in an amount sufficient to increase the intensity of flavor of the at least one cooling compound and increase the intensity of the cooling sensation of the at least one cooling compound, when a subject is contacted with the composition.

One aspect presented herein provides a flavored article comprising
  a) the composition according to some aspects presented herein; and
  b) an orally acceptable carrier.

In one aspect, the at least one cooling compound is selected from the group consisting of: menthol, menthone, isopulegol, N-ethyl p-menthanecarboxamide (WS-3), N,2,3-trimethyl-2-isopropylbutanamide (WS-23), ethyl N-[[5-methyl-2-(isopropyl)cyclohexyl]carbonyl]glycinate, menthyl lactate, menthone glycerine acetal (Frescolat® MGA), mono-menthyl succinate (Physcool®), mono-menthyl glutarate, O-menthyl glycerine (CoolAct® 10) and 2-sec-butyl-cyclohexanone (Freskomenthe®), menthane, camphor, pulegol, cineol, mint oil, peppermint oil, spearmint oil, eucalyptus oil, 3-1-menthoxypropane-1,2-diol, 3-1-menthoxy-2-methylpropane-1,2-diol, p-menthane-3,8-diol, 2-1-menthoxyethane-1-ol, 3-1-menthoxypropane-1-ol, and 4-1-menthoxybutane-1-ol.

In one aspect, the amount sufficient of the at least one compound is from 1 to 10,000 ppm.

In one aspect, the amount sufficient of the at least one potentiating agent is from 50 to 5,000 ppm.

In one aspect, the amount sufficient of the at least one potentiating agent is from 0.2 to 20 ppm.

In one aspect, the composition comprises:
  a) at least one cooling compound;
  b) a mixture of potentiating agents comprising methyl acetate and at least one other potentiating agent selected from the group consisting of: (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, a mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[3,2-g]chromen-7-one, at least one polymethoxy flavonoid, 3-(1-((3,5-dimethylisoxazol-4-yl)methyl)-1H-pyrazol-4-yl)-1-(3-hydroxybenzyl)imidazolidine-2,4-dione, and combinations thereof, wherein the mixture is present in the composition in an amount sufficient to increase the intensity of flavor of the at least one cooling compound and increase the intensity of the cooling sensation of the at least one cooling compound, when a subject is contacted with the composition.

In one aspect, the amount sufficient of the mixture is from 1 to 10,000 ppm.

In one aspect, the amount sufficient of the mixture is from 50 to 5,000 ppm.

In one aspect, the amount sufficient of the mixture is from 0.2 to 20 ppm.

In one aspect the ratio of the methyl acetate to the at least one other potentiating agent in the mixture is from 1:0.00001 to 1:10.

In one aspect the ratio of the methyl acetate to the at least one other potentiating agent in the mixture is from 1:0.0001 to 1:1.

In one aspect the ratio of the methyl acetate to the at least one other potentiating agent in the mixture is from 1:0.005 to 1:0.1.

In one aspect, the mixture comprises methyl acetate and 3-(1-((3,5-dimethylisoxazol-4-yl)methyl)-1H-pyrazol-4-yl)-1-(3-hydroxybenzyl)imidazolidine-2,4-dione.

One aspect presented herein provides a method,
wherein the method provides a cooling sensation to a subject in need thereof,
wherein the method comprises contacting the subject with a composition according to some aspects presented herein,
wherein the method increases the intensity of the cooling effect of the at least one cooling compound perceived by the subject, compared to the intensity of the cooling effect perceived by a subject contacted with a composition lacking the at least one potentiating agent, and
wherein the method increases the intensity of the flavor of the at least one cooling compound perceived by the subject, compared to the intensity of the flavor of the at least one cooling compound perceived by a subject contacted with a composition lacking the at least one potentiating agent.

One aspect presented herein provides a method,
wherein the method provides a cooling sensation to a subject in need thereof,
wherein the method comprises contacting the subject with a product according to some aspects presented herein,
wherein the method increases the intensity of the cooling effect of the at least one cooling compound perceived by the subject, compared to the intensity of the cooling effect perceived by a subject contacted with a product lacking the at least one potentiating agent, and
wherein the method increases the intensity of the flavor of the at least one cooling compound perceived by the subject, compared to the intensity of the flavor of the at least one cooling compound perceived by a subject contacted with a product lacking the at least one potentiating agent.

DETAILED DESCRIPTION

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

The present disclosure provides personal care products intended for use on the oral cavity and flavor compositions for use in such personal care products, comprising cooling compounds combined with one or more compounds that potentiate the flavor, cooling and refreshing sensation provided by the cooling compounds.

In alternate aspects, the present disclosure provides flavored articles and flavor compositions for use in such flavored articles, comprising cooling compounds combined with one or more compounds that potentiate the flavor, cooling and refreshing sensation provided by the cooling compounds.

A flavored article includes, for example, a food product (e.g., a beverage), a sweetener such as a natural sweetener or an artificial sweetener, a pharmaceutical composition, a dietary supplement, a nutraceutical, a dental hygienic composition and a cosmetic product. The flavored article may further contain a flavoring.

In some aspects, the flavored article is a food product including, for example, but not limited to, fruits, vegetables, juices, meat products such as ham, bacon and sausage, egg products, fruit concentrates, gelatins and gelatin-like products such as jams, jellies, preserves and the like, milk products such as ice cream, sour cream and sherbet, icings, syrups including molasses, corn, wheat, rye, soybean, oat, rice and barley products, nut meats and nut products, cakes, cookies, confectioneries such as candies, gums, fruit flavored drops, and chocolates, chewing gums, mints, creams, pies and breads.

In some aspects, the food product is a beverage including, for example, but not limited to, coffee, tea, carbonated soft drinks, such as COKE and PEPSI, non-carbonated soft drinks and other fruit drinks, sports drinks such as GATORADE and alcoholic beverages such as beers, wines and liquors.

A flavored article may also include prepared packaged products, such as granulated flavor mixes, which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like.

A flavored article may also include diet or low-calorie food and beverages containing little or no sucrose. Flavored articles may also include condiments such as herbs, spices and seasonings, flavor enhancers (e.g., monosodium glutamate), dietetic sweeteners and liquid sweeteners.

In some aspects, the flavored article is a pharmaceutical composition, a dietary supplement, a nutraceutical, a dental hygienic composition or a cosmetic product.

Dental hygiene compositions are known in the art and include, for example, but not limited to, a toothpaste, a mouthwash, a plaque rinse, a dental floss, a dental pain reliever (such as ANBESOL), a tooth polish, a dental gel, a dental spray, a dental powder, and the like. In some aspects, the dental hygiene composition includes one natural sweetener. In some aspects, the dental hygiene composition includes more than one natural sweetener. In some aspects, the dental hygiene composition includes one synthetic sweetener. In some aspects, the dental hygiene composition includes more than one synthetic sweetener. In some aspects, the dental hygiene composition includes sucrose and corn syrup, or sucrose and aspartame.

In some aspects, a cosmetic product includes, for example, but not limited to, a face cream, a lipstick, a lip gloss and the like. Other suitable cosmetic products of use in this disclosure include a lip balm, such as CHAPSTICK or BURT'S BEESWAX Lip Balm. Accordingly, some aspects presented herein provide a composition, comprising:
- a) at least one cooling compound;
- b) at least one potentiating agent selected from the group consisting of: methyl acetate, (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, a mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[3,2-g]chromen-7-one, at least one polymethoxy flavonoid, 3-(1-((3,5-dimethylisoxazol-4-yl)methyl)-1H-pyrazol-4-yl)-1-(3-hydroxybenzyl)imidazolidine-2,4-dione, and combinations thereof;
  - wherein the at least one potentiating agent is present in the composition in an amount sufficient to increase the intensity of flavor of the at least one cooling compound and increase the intensity of the cooling sensation of the at least one cooling compound, when a subject is contacted with the composition.

In some aspects, the amount sufficient of the at least one potentiating agent is from 0.02 to 10,000 ppm.

In some aspects, the amount sufficient of the at least one potentiating agent is from 1 to 10,000 ppm.

In some aspects, the amount sufficient of the at least one potentiating agent is from 50 to 5,000 ppm.

In some aspects, the amount sufficient of the at least one potentiating agent is from 100 to 2,000 ppm.

In some aspects, the amount sufficient of the at least one potentiating agent is from 0.1 to 1,000 ppm.

In some aspects, the amount sufficient of the at least one potentiating agent is from 0.02 to 100 ppm.

In some aspects, the amount sufficient of the at least one potentiating agent is from 0.2 to 20 ppm.

In some aspects, the amount sufficient of the at least one potentiating agent is from 0.02 to 10,000 ppm. In some aspects, the amount sufficient of the at least one potentiating agent is from 0.04 to 10,000 ppm. In some aspects, the amount sufficient of the at least one potentiating agent is from 0.06 to 10,000 ppm. In some aspects, the amount sufficient of the at least one potentiating agent is from 0.08 to 10,000 ppm. In some aspects, the amount sufficient of the at least one potentiating agent is from 0.1 to 10,000 ppm. In some aspects, the amount sufficient of the at least one potentiating agent is from 0.2 to 10,000 ppm. In some aspects, the amount sufficient of the at least one potentiating agent is from 0.3 to 10,000 ppm. In some aspects, the amount sufficient of the at least one potentiating agent is from 0.4 to 10,000 ppm. In some aspects, the amount sufficient of the at least one potentiating agent is from 0.5 to 10,000 ppm. In some aspects, the amount sufficient of the at least one potentiating agent is from 0.6 to 10,000 ppm. In some aspects, the amount sufficient of the at least one potentiating agent is from 0.7 to 10,000 ppm. In some aspects, the amount sufficient of the at least one potentiating agent is from 0.8 to 10,000 ppm. In some aspects, the amount sufficient of the at least one potentiating agent is from 0.9 to 10,000 ppm. In some aspects, the amount sufficient of the at least one potentiating agent is from 1 to 10,000 ppm. In some aspects, the amount sufficient of the at least one potentiating agent is from 2 to 10,000 ppm. In some aspects, the amount sufficient of the at least one potentiating agent is from 3 to 10,000 ppm. In some aspects, the amount sufficient of the at least one potentiating agent is from 4 to 10,000 ppm. In some aspects, the amount sufficient of the at least one potentiating agent is from 5 to 10,000 ppm. In some aspects, the amount sufficient of the at least one potentiating agent is from 6 to 10,000 ppm. In some aspects, the amount sufficient of the at least one potentiating agent is from 7 to 10,000 ppm. In some aspects, the amount sufficient of the at least one potentiating agent is from 8 to 10,000 ppm. In some aspects, the amount sufficient of the at least one potentiating agent is from 9 to 10,000 ppm. In some aspects, the amount sufficient of the at least one potentiating agent is from 10 to 10,000 ppm. In some aspects, the amount sufficient of the at least one potentiating agent is from 20 to 10,000 ppm. In some aspects, the amount sufficient of the at least one potentiating agent is from 30 to 10,000 ppm. In some aspects, the amount sufficient of the at least one potentiating agent is from 40 to 10,000 ppm. In some aspects, the amount sufficient of the at least one potentiating agent is from 50 to 10,000 ppm. In some aspects, the amount sufficient of the at least one potentiating agent is from 60 to 10,000 ppm. In some aspects, the amount sufficient of the at least one potentiating agent is from 70 to 10,000 ppm. In some aspects, the amount sufficient of the at least one potentiating agent is from 80 to 10,000 ppm. In some aspects, the amount sufficient of the at least one potentiating agent is from 90 to 10,000 ppm. In some aspects, the amount sufficient of the at least one potentiating agent is from 100 to 10,000 ppm. In some aspects, the amount sufficient of the at least one potentiating agent is from 200 to 10,000 ppm. In some aspects, the amount sufficient of the at least one potentiating agent is from 300 to 10,000 ppm. In some aspects, the amount sufficient of the at least one potentiating agent is from 400 to 10,000 ppm. In some aspects, the amount sufficient of the at least one potentiating agent is from 500 to 10,000 ppm. In some aspects, the amount sufficient of the at least one potentiating agent is from 600 to 10,000 ppm. In some aspects, the amount sufficient of the at least one potentiating agent is from 700 to 10,000 ppm. In some aspects, the amount sufficient of the at least one potentiating agent is from 800 to 10,000 ppm. In some aspects, the amount sufficient of the at least one potentiating agent is from 900 to 10,000 ppm. In some aspects, the amount sufficient of the at least one potentiating agent is from 1,000 to 10,000 ppm. In some aspects, the amount sufficient of the at least one potentiating agent is from 2,000 to 10,000 ppm. In some aspects, the amount sufficient of the at least one potentiating agent is from 3,000 to 10,000 ppm. In some aspects, the amount sufficient of the at least one potentiating agent is from 4,000 to 10,000 ppm. In some aspects, the amount sufficient of the at least one potentiating agent is from 5,000 to 10,000 ppm. In some aspects, the amount sufficient of the at least one potentiating agent is from 6,000 to 10,000 ppm. In some aspects, the amount sufficient of the at least one potentiating agent is from 7,000 to 10,000 ppm. In some aspects, the amount sufficient of the at least one potentiating agent is from 8,000 to 10,000 ppm. In some aspects, the amount sufficient of the at least one potentiating agent is from 9,000 to 10,000 ppm.

In some aspects, the amount sufficient of the at least one potentiating agent is 0.02, or 0.04, or 0.06, or 0.08, or 0.10, or 0.20, or 0.30, or 0.40, or 0.50, or 0.60, or 0.70, or 0.80, or 0.90, or 1, or 2, or 3, or 4, or 5, or 6, or 7, or 8, or 9, or 10, or 20, or 30, or 40, or 50, or 60, or 70, or 80, or 90, or 100, or 200, or 300, or 400, or 500, or 600, or 700, or 800, or 900, or 1,000, or 2,000, or 3,000, or 4,000, or 5,000, or 6,000, or 7,000, or 8,000, or 9,000, or 10,000 ppm.

In some aspects, the at least one potentiating agent is methyl acetate. In some aspects, the amount sufficient of the methyl acetate is from 0.00001 to 10% of the composition. In some aspects, the amount sufficient of the methyl acetate is from 0.005 to 0.5% of the composition. In some aspects, the amount sufficient of the methyl acetate is from 0.001 to 0.2% of the composition.

In some aspects, the amount sufficient of the methyl acetate is from 0.00002 to 10% of the composition. In some aspects, the amount sufficient of the methyl acetate is from 0.00004 to 10% of the composition. In some aspects, the amount sufficient of the methyl acetate is from 0.00006 to 10% of the composition. In some aspects, the amount sufficient of the methyl acetate is from 0.00008 to 10% of the composition. In some aspects, the amount sufficient of the methyl acetate is from 0.0001 to 10% of the composition. In some aspects, the amount sufficient of the methyl acetate is from 0.0002 to 10% of the composition. In some aspects, the amount sufficient of the methyl acetate is from 0.0004 to 10% of the composition. In some aspects, the amount sufficient of the methyl acetate is from 0.0006 to 10% of the composition. In some aspects, the amount sufficient of the methyl acetate is from 0.0008 to 10% of the composition. In some aspects, the amount sufficient of the methyl acetate is from 0.001 to 10% of the composition. In some aspects, the amount sufficient of the methyl acetate is from 0.002 to 10% of the composition. In some aspects, the amount sufficient of the methyl acetate is from 0.003 to 10% of the composition. In some aspects, the amount sufficient of the methyl acetate is from 0.004 to 10% of the composition. In some aspects, the amount sufficient of the methyl acetate is from 0.005 to 10% of the composition. In some aspects, the amount sufficient of the methyl acetate is from 0.006 to 10% of the composition. In some aspects, the amount sufficient of the methyl acetate is from 0.007 to 10% of the composition. In some aspects, the amount sufficient of the methyl acetate is from 0.008 to 10% of the composition. In some aspects, the amount sufficient of the methyl acetate is from 0.009 to 10% of the composition. In some aspects, the amount sufficient of the methyl acetate is from 0.01 to 10% of the composition. In some aspects, the amount sufficient of the methyl acetate is from 0.02 to 10% of the composition. In some aspects, the amount sufficient of the methyl acetate is from 0.03 to 10% of the composition. In some aspects, the amount sufficient of the methyl acetate is from 0.04 to 10% of the composition. In some aspects, the amount sufficient of the methyl acetate is from 0.05 to 10% of the composition. In some aspects, the amount sufficient of the methyl acetate is from 0.06 to 10% of the composition. In some aspects, the amount sufficient of the methyl acetate is from 0.07 to 10% of the composition. In some aspects, the amount sufficient of the methyl acetate is from 0.08 to 10% of the composition. In some aspects, the amount sufficient of the methyl acetate is from 0.09 to 10% of the composition. In some aspects, the amount sufficient of the methyl acetate is from 0.1 to 10% of the composition. In some aspects, the amount sufficient of the methyl acetate is from 0.2 to 10% of the composition. In some aspects, the amount sufficient of the methyl acetate is from 0.3 to 10% of the composition. In some aspects, the amount sufficient of the methyl acetate is from 0.4 to 10% of the composition. In some aspects, the amount sufficient of the methyl acetate is from 0.5 to 10% of the composition. In some aspects, the amount sufficient of the methyl acetate is from 0.6 to 10% of the composition. In some aspects, the amount sufficient of the methyl acetate is from 0.7 to 10% of the composition. In some aspects, the amount sufficient of the methyl acetate is from 0.8 to 10% of the composition. In some aspects, the amount sufficient of the methyl acetate is from 0.9 to 10% of the composition. In some aspects, the amount sufficient of the methyl acetate is from 1 to 10% of the composition. In some aspects, the amount sufficient of the methyl acetate is from 2 to 10% of the composition. In some aspects, the amount sufficient of the methyl acetate is from 3 to 10% of the composition. In some aspects, the amount sufficient of the methyl acetate is from 4 to 10% of the composition. In some aspects, the amount sufficient of the methyl acetate is from 5 to 10% of the composition. In some aspects, the amount sufficient of the methyl acetate is from 6 to 10% of the composition. In some aspects, the amount sufficient of the methyl acetate is from 7 to 10% of the composition. In some aspects, the amount sufficient of the methyl acetate is from 8 to 10% of the composition. In some aspects, the amount sufficient of the methyl acetate is from 9 to 10% of the composition.

In some aspects, the at least one potentiating agent is (+)-methyl(1R)-cis-3-oxo-2-pentyl-1-cyclopentaneacetate. In some aspects, the amount sufficient of the (+)-methyl (1R)-cis-3-oxo-2-pentyl-1-cyclopentaneacetate is from 0.00001 to 10% of the composition. In some aspects, the amount sufficient of the (+)-methyl(1R)-cis-3-oxo-2-pentyl-1-cyclopentaneacetate is from 0.005 to 0.5% of the composition.

In some aspects, the amount sufficient of the (+)-methyl (1R)-cis-3-oxo-2-pentyl-1-cyclopentaneacetate is from 0.00002 to 10% of the composition. In some aspects, the amount sufficient of the (+)-methyl(1R)-cis-3-oxo-2-pentyl-1-cyclopentaneacetate is from 0.00004 to 10% of the composition. In some aspects, the amount sufficient of the (+)-methyl(1R)-cis-3-oxo-2-pentyl-1-cyclopentaneacetate is from 0.00006 to 10% of the composition. In some aspects, the amount sufficient of the (+)-methyl(1R)-cis-3-oxo-2-pentyl-1-cyclopentaneacetate is from 0.00008 to 10% of the composition. In some aspects, the amount sufficient of the (+)-methyl(1R)-cis-3-oxo-2-pentyl-1-cyclopentaneacetate is from 0.0001 to 10% of the composition. In some aspects, the amount sufficient of the (+)-methyl(1R)-cis-3-oxo-2-pentyl-1-cyclopentaneacetate is from 0.0002 to 10% of the composition. In some aspects, the amount sufficient of the (+)-methyl(1R)-cis-3-oxo-2-pentyl-1-cyclopentaneacetate is from 0.0004 to 10% of the composition. In some aspects, the amount sufficient of the (+)-methyl(1R)-cis-3-oxo-2-pentyl-1-cyclopentaneacetate is from 0.0006 to 10% of the composition. In some aspects, the amount sufficient of the (+)-methyl(1R)-cis-3-oxo-2-pentyl-1-cyclopentaneacetate is from 0.0008 to 10% of the composition. In some aspects, the amount sufficient of the (+)-methyl(1R)-cis-3-oxo-2-pentyl-1-cyclopentaneacetate is from 0.001 to 10% of the composition. In some aspects, the amount sufficient of the (+)-methyl(1R)-cis-3-oxo-2-pentyl-1-cyclopentaneacetate is from 0.002 to 10% of the composition. In some aspects, the amount sufficient of the (+)-methyl(1R)-cis-3-oxo-2-pentyl-1-cyclopentaneacetate is from 0.003 to 10% of the composition. In some aspects, the amount sufficient of the (+)-methyl(1R)-cis-3-oxo-2-pentyl-1-cyclopentaneacetate is from 0.004 to 10% of the composition. In some aspects, the amount sufficient of the (+)-methyl(1R)-cis-3-oxo-2-pentyl-1-cyclopentaneacetate is from 0.005 to 10% of the composition. In some aspects, the amount sufficient of the (+)-methyl(1R)-cis-3-oxo-2-pentyl-1-cyclopentaneacetate is from 0.006 to 10% of the composition. In some aspects, the amount sufficient of the (+)-methyl(1R)-cis-3-oxo-2-pentyl-1-cyclopentaneacetate is from 0.007 to 10% of the composition. In some aspects, the amount sufficient of the (+)-methyl(1R)-cis-3-oxo-2-pentyl-1-cyclopentaneacetate is from 0.008 to 10% of the composition. In some aspects, the amount sufficient of the (+)-methyl(1R)-cis-3-oxo-2-pentyl-1-cyclopentaneacetate is from 0.009 to 10% of the composition. In some aspects, the amount sufficient of the (+)-methyl(1R)-cis-3-oxo-2-pentyl-1-cyclopentaneacetate is from 0.01 to 10% of the composition. In some aspects, the amount sufficient of the (+)-methyl(1R)-cis-3-oxo-2-pentyl-1-cyclopentaneacetate is from 0.02 to 10% of the composition. In some aspects, the amount sufficient of the (+)-methyl(1R)-cis-3-oxo-2-pentyl-1-cyclopentaneacetate is from 0.03 to 10% of the composition. In some aspects, the amount sufficient of the (+)-methyl(1R)-cis-3-oxo-2-pentyl-1-cyclopentaneacetate is from 0.04 to 10% of the composition. In some aspects, the amount sufficient of the (+)-methyl(1R)-cis-3-oxo-2-pentyl-1-cyclopentaneacetate is from 0.05 to 10% of the composition. In some aspects, the amount sufficient of the (+)-methyl(1R)-cis-3-oxo-2-pentyl-1-cyclopentaneacetate is from 0.06 to 10% of the composition. In some aspects, the amount sufficient of the (+)-methyl(1R)-cis-3-oxo-2-pentyl-1-cyclopentaneacetate is from 0.07 to 10% of the composition. In some aspects, the amount sufficient of the (+)-methyl(1R)-cis-3-oxo-2-pentyl-1-cyclopentaneacetate is from 0.08 to 10% of the composition. In some aspects, the amount sufficient of the (+)-methyl(1R)-cis-3-oxo-2-pentyl-1-cyclopentaneacetate is from 0.09 to 10% of the composition. In some aspects, the amount sufficient of the (+)-methyl(1R)-cis-3-oxo-2-pentyl-1-cyclopentaneacetate is from 0.1 to 10% of the composition. In some aspects, the amount sufficient of the (+)-methyl(1R)-cis-3-oxo-2-pentyl-1-cyclopentaneacetate is from 0.2 to 10% of the composition. In some aspects, the amount sufficient of the (+)-methyl(1R)-cis-3-oxo-2-pentyl-1-cyclopentaneacetate is from 0.3 to 10% of the composition. In some aspects, the amount sufficient of the (+)-methyl(1R)-cis-3-oxo-2-pentyl-1-cyclopentaneacetate is from 0.4 to 10% of the composition. In some aspects, the amount sufficient of the (+)-methyl(1R)-cis-3-oxo-2-pentyl-1-cyclopentaneacetate is from 0.5 to 10% of the composition. In some aspects, the amount sufficient of the (+)-methyl(1R)-cis-3-oxo-2-pentyl-1-cyclopentaneacetate is from 0.6 to 10% of the composition. In some aspects, the amount sufficient of the (+)-methyl(1R)-cis-3-oxo-2-pentyl-1-cyclopentaneacetate is from 0.7 to 10% of the composition. In some aspects, the amount sufficient of the (+)-methyl(1R)-cis-3-oxo-2-pentyl-1-cyclopentaneacetate is from 0.8 to 10% of the composition. In some aspects, the amount sufficient of the (+)-methyl(1R)-cis-3-oxo-2-pentyl-1-cyclopentaneacetate is from 0.9 to 10% of the composition. In some aspects, the amount sufficient of the (+)-methyl(1R)-cis-3-oxo-2-pentyl-1-cyclopentaneacetate is from 1 to 10% of the composition. In some aspects, the amount sufficient of the (+)-methyl(1R)-cis-3-oxo-2-pentyl-1-cyclopentaneacetate is from 2 to 10% of the composition. In some aspects, the amount sufficient of the (+)-methyl(1R)-cis-3-oxo-2-pentyl-1-cyclopentaneacetate is from 3 to 10% of the composition. In some aspects, the amount sufficient of the (+)-methyl(1R)-cis-3-oxo-2-pentyl-1-cyclopentaneacetate is from 4 to 10% of the composition. In some aspects, the amount sufficient of the (+)-methyl(1R)-cis-3-oxo-2-pentyl-1-cyclopentaneacetate is from 5 to 10% of the composition. In some aspects, the amount sufficient of the (+)-methyl(1R)-cis-3-oxo-2-pentyl-1-cyclopentaneacetate is from 6 to 10% of the composition. In some aspects, the amount sufficient of the (+)-methyl(1R)-cis-3-oxo-2-pentyl-1-cyclopentaneacetate is from 7 to 10% of the composition. In some aspects, the amount sufficient of the (+)-methyl(1R)-cis-3-oxo-2-pentyl-1-cyclopentaneacetate is from 8 to 10% of the composition. In some aspects, the amount sufficient of the (+)-methyl(1R)-cis-3-oxo-2-pentyl-1-cyclopentaneacetate is from 9 to 10% of the composition.

In some aspects, the at least one potentiating agent is phloretin. In some aspects, the amount sufficient of the phloretin is from 0.00001 to 10% of the composition. In some aspects, the amount sufficient of the phloretin is from 0.005 to 0.5% of the composition.

In some aspects, the amount sufficient of the phloretin is from 0.00002 to 10% of the composition. In some aspects, the amount sufficient of the phloretin is from 0.00004 to 10% of the composition. In some aspects, the amount sufficient of the phloretin is from 0.00006 to 10% of the composition. In some aspects, the amount sufficient of the phloretin is from 0.00008 to 10% of the composition. In some aspects, the amount sufficient of the phloretin is from 0.0001 to 10% of the composition. In some aspects, the amount sufficient of the phloretin is from 0.0002 to 10% of the composition. In some aspects, the amount sufficient of the phloretin is from 0.0004 to 10% of the composition. In some aspects, the amount sufficient of the phloretin is from 0.0006 to 10% of the composition. In some aspects, the amount sufficient of the phloretin is from 0.0008 to 10% of the composition. In some aspects, the amount sufficient of the phloretin is from 0.001 to 10% of the composition. In some aspects, the amount sufficient of the phloretin is from 0.002 to 10% of the composition. In some aspects, the amount sufficient of the phloretin is from 0.003 to 10% of the composition. In some aspects, the amount sufficient of the phloretin is from 0.004 to 10% of the composition. In some aspects, the amount sufficient of the phloretin is from 0.005 to 10% of the composition. In some aspects, the amount sufficient of the phloretin is from 0.006 to 10% of the composition. In some aspects, the amount sufficient of the phloretin is from 0.007 to 10% of the composition. In some aspects, the amount sufficient of the phloretin is from 0.008 to 10% of the composition. In some aspects, the amount sufficient of the phloretin is from 0.009 to 10% of the composition. In some aspects, the amount sufficient of the phloretin is from 0.01 to 10% of the composition. In some aspects, the amount sufficient of the phloretin is from 0.02 to 10% of the composition. In some aspects, the amount sufficient of the phloretin is from 0.03 to 10% of the composition. In some aspects, the amount sufficient of the phloretin is from 0.04 to 10% of the composition. In some aspects, the amount sufficient of the phloretin is from 0.05 to 10% of the composition. In some aspects, the amount sufficient of the phloretin is from 0.06 to 10% of the composition. In some aspects, the amount sufficient of the phloretin is from 0.07 to 10% of the composition. In some aspects, the amount sufficient of the phloretin is from 0.08 to 10% of the composition. In some aspects, the amount sufficient of the phloretin is from 0.09 to 10% of the composition. In some aspects, the amount sufficient of the phloretin is from 0.1 to 10% of the composition. In some aspects, the amount sufficient of the phloretin is from 0.2 to 10% of the composition. In some aspects, the amount sufficient of the phloretin is from 0.3 to 10% of the composition. In some aspects, the amount sufficient of the phloretin is from 0.4 to 10% of the composition. In some aspects, the amount sufficient of the phloretin is from 0.5 to 10% of the composition. In some aspects, the amount sufficient of the phloretin is from 0.6 to 10% of the composition. In some aspects, the amount sufficient of the phloretin is from 0.7 to 10% of the composition. In some aspects, the amount sufficient of the phloretin is from 0.8 to 10% of the composition. In some aspects, the amount sufficient of the phloretin is from 0.9 to 10% of the composition. In some aspects, the amount sufficient of the phloretin is from 1 to 10% of the composition. In some aspects, the amount sufficient of the phloretin is from 2 to 10% of the composition. In some aspects, the amount sufficient of the phloretin is from 3 to 10% of the composition. In some aspects, the amount sufficient of the phloretin is from 4 to 10% of the composition. In some aspects, the amount sufficient of the phloretin is from 5 to 10% of the composition.

In some aspects, the amount sufficient of the phloretin is from 6 to 10% of the composition. In some aspects, the amount sufficient of the phloretin is from 7 to 10% of the composition. In some aspects, the amount sufficient of the phloretin is from 8 to 10% of the composition. In some aspects, the amount sufficient of the phloretin is from 9 to 10% of the composition.

In some aspects, the at least one potentiating agent is n-(1-propylbutyl)-1,3-benzodioxole-5-carboxamide. In some aspects, the amount sufficient of the n-(1-propylbutyl)-1,3-benzodioxole-5-carboxamide is from 0.00001 to 10% of the composition.

In some aspects, the amount sufficient of the n-(1-propylbutyl)-1,3-benzodioxole-5-carboxamide is from 0.005 to 0.5% of the composition.

In some aspects, the amount sufficient of the n-(1-propylbutyl)-1,3-benzodioxole-5-carboxamide is from 0.00002 to 10% of the composition. In some aspects, the amount sufficient of the n-(1-propylbutyl)-1,3-benzodioxole-5-carboxamide is from 0.00004 to 10% of the composition. In some aspects, the amount sufficient of the n-(1-propylbutyl)-1,3-benzodioxole-5-carboxamide is from 0.00006 to 10% of the composition. In some aspects, the amount sufficient of the n-(1-propylbutyl)-1,3-benzodioxole-5-carboxamide is from 0.00008 to 10% of the composition. In some aspects, the amount sufficient of the n-(1-propylbutyl)-1,3-benzodioxole-5-carboxamide is from 0.0001 to 10% of the composition. In some aspects, the amount sufficient of the n-(1-propylbutyl)-1,3-benzodioxole-5-carboxamide is from 0.0002 to 10% of the composition. In some aspects, the amount sufficient of the n-(1-propylbutyl)-1,3-benzodioxole-5-carboxamide is from 0.0004 to 10% of the composition. In some aspects, the amount sufficient of the n-(1-propylbutyl)-1,3-benzodioxole-5-carboxamide is from 0.0006 to 10% of the composition. In some aspects, the amount sufficient of the n-(1-propylbutyl)-1,3-benzodioxole-5-carboxamide is from 0.0008 to 10% of the composition. In some aspects, the amount sufficient of the n-(1-propylbutyl)-1,3-benzodioxole-5-carboxamide is from 0.001 to 10% of the composition. In some aspects, the amount sufficient of the n-(1-propylbutyl)-1,3-benzodioxole-5-carboxamide is from 0.002 to 10% of the composition. In some aspects, the amount sufficient of the n-(1-propylbutyl)-1,3-benzodioxole-5-carboxamide is from 0.003 to 10% of the composition. In some aspects, the amount sufficient of the n-(1-propylbutyl)-1,3-benzodioxole-5-carboxamide is from 0.004 to 10% of the composition. In some aspects, the amount sufficient of the n-(1-propylbutyl)-1,3-benzodioxole-5-carboxamide is from 0.005 to 10% of the composition. In some aspects, the amount sufficient of the n-(1-propylbutyl)-1,3-benzodioxole-5-carboxamide is from 0.006 to 10% of the composition. In some aspects, the amount sufficient of the n-(1-propylbutyl)-1,3-benzodioxole-5-carboxamide is from 0.007 to 10% of the composition. In some aspects, the amount sufficient of the n-(1-propylbutyl)-1,3-benzodioxole-5-carboxamide is from 0.008 to 10% of the composition. In some aspects, the amount sufficient of the n-(1-propylbutyl)-1,3-benzodioxole-5-carboxamide is from 0.009 to 10% of the composition. In some aspects, the amount sufficient of the n-(1-propylbutyl)-1,3-benzodioxole-5-carboxamide is from 0.01 to 10% of the composition. In some aspects, the amount sufficient of the n-(1-propylbutyl)-1,3-benzodioxole-5-carboxamide is from 0.02 to 10% of the composition. In some aspects, the amount sufficient of the n-(1-propylbutyl)-1,3-benzodioxole-5-carboxamide is from 0.03 to 10% of the composition. In some aspects, the amount sufficient of the n-(1-propylbutyl)-1,3-benzodioxole-5-carboxamide is from 0.04 to 10% of the composition. In some aspects, the amount sufficient of the n-(1-propylbutyl)-1,3-benzodioxole-5-carboxamide is from 0.05 to 10% of the composition. In some aspects, the amount sufficient of the n-(1-propylbutyl)-1,3-benzodioxole-5-carboxamide is from 0.06 to 10% of the composition. In some aspects, the amount sufficient of the n-(1-propylbutyl)-1,3-benzodioxole-5-carboxamide is from 0.07 to 10% of the composition. In some aspects, the amount sufficient of the n-(1-propylbutyl)-1,3-benzodioxole-5-carboxamide is from 0.08 to 10% of the composition. In some aspects, the amount sufficient of the n-(1-propylbutyl)-1,3-benzodioxole-5-carboxamide is from 0.09 to 10% of the composition. In some aspects, the amount sufficient of the n-(1-propylbutyl)-1,3-benzodioxole-5-carboxamide is from 0.1 to 10% of the composition. In some aspects, the amount sufficient of the n-(1-propylbutyl)-1,3-benzodioxole-5-carboxamide is from 0.2 to 10% of the composition. In some aspects, the amount sufficient of the n-(1-propylbutyl)-1,3-benzodioxole-5-carboxamide is from 0.3 to 10% of the composition. In some aspects, the amount sufficient of the n-(1-propylbutyl)-1,3-benzodioxole-5-carboxamide is from 0.4 to 10% of the composition. In some aspects, the amount sufficient of the n-(1-propylbutyl)-1,3-benzodioxole-5-carboxamide is from 0.5 to 10% of the composition. In some aspects, the amount sufficient of the n-(1-propylbutyl)-1,3-benzodioxole-5-carboxamide is from 0.6 to 10% of the composition. In some aspects, the amount sufficient of the n-(1-propylbutyl)-1,3-benzodioxole-5-carboxamide is from 0.7 to 10% of the composition. In some aspects, the amount sufficient of the n-(1-propylbutyl)-1,3-benzodioxole-5-carboxamide is from 0.8 to 10% of the composition. In some aspects, the amount sufficient of the n-(1-propylbutyl)-1,3-benzodioxole-5-carboxamide is from 0.9 to 10% of the composition. In some aspects, the amount sufficient of the n-(1-propylbutyl)-1,3-benzodioxole-5-carboxamide is from 1 to 10% of the composition. In some aspects, the amount sufficient of the n-(1-propylbutyl)-1,3-benzodioxole-5-carboxamide is from 2 to 10% of the composition. In some aspects, the amount sufficient of the n-(1-propylbutyl)-1,3-benzodioxole-5-carboxamide is from 3 to 10% of the composition. In some aspects, the amount sufficient of the n-(1-propylbutyl)-1,3-benzodioxole-5-carboxamide is from 4 to 10% of the composition. In some aspects, the amount sufficient of the n-(1-propylbutyl)-1,3-benzodioxole-5-carboxamide is from 5 to 10% of the composition. In some aspects, the amount sufficient of the n-(1-propylbutyl)-1,3-benzodioxole-5-carboxamide is from 6 to 10% of the composition. In some aspects, the amount sufficient of the n-(1-propylbutyl)-1,3-benzodioxole-5-carboxamide is from 7 to 10% of the composition. In some aspects, the amount sufficient of the n-(1-propylbutyl)-1,3-benzodioxole-5-carboxamide is from 8 to 10% of the composition. In some aspects, the amount sufficient of the n-(1-propylbutyl)-1,3-benzodioxole-5-carboxamide is from 9 to 10% of the composition.

In some aspects, the at least one potentiating agent is ferulic acid. In some aspects, the amount sufficient of the ferulic acid is from 0.00001 to 10% of the composition. In some aspects, the amount sufficient of the ferulic acid is from 0.005 to 0.5% of the composition. In some aspects, the amount sufficient of the ferulic acid is from 0.0005 to 0.1% of the composition.

In some aspects, the amount sufficient of the ferulic acid is from 0.00002 to 10% of the composition. In some aspects, the amount sufficient of the ferulic acid is from 0.00004 to 10% of the composition. In some aspects, the amount sufficient of the ferulic acid is from 0.00006 to 10% of the composition. In some aspects, the amount sufficient of the ferulic acid is from 0.00008 to 10% of the composition. In some aspects, the amount sufficient of the ferulic acid is from 0.0001 to 10% of the composition. In some aspects, the amount sufficient of the ferulic acid is from 0.0002 to 10% of the composition. In some aspects, the amount sufficient of the ferulic acid is from 0.0004 to 10% of the composition. In some aspects, the amount sufficient of the ferulic acid is from 0.0006 to 10% of the composition. In some aspects, the amount sufficient of the ferulic acid is from 0.0008 to 10% of the composition. In some aspects, the amount sufficient of the ferulic acid is from 0.001 to 10% of the composition. In some aspects, the amount sufficient of the ferulic acid is from 0.002 to 10% of the composition. In some aspects, the amount sufficient of the ferulic acid is from 0.003 to 10% of the composition. In some aspects, the amount sufficient of the ferulic acid is from 0.004 to 10% of the composition. In some aspects, the amount sufficient of the ferulic acid is from 0.005 to 10% of the composition. In some aspects, the amount sufficient of the ferulic acid is from 0.006 to 10% of the composition. In some aspects, the amount sufficient of the ferulic acid is from 0.007 to 10% of the composition. In some aspects, the amount sufficient of the ferulic acid is from 0.008 to 10% of the composition. In some aspects, the amount sufficient of the ferulic acid is from 0.009 to 10% of the composition. In some aspects, the amount sufficient of the ferulic acid is from 0.01 to 10% of the composition. In some aspects, the amount sufficient of the ferulic acid is from 0.02 to 10% of the composition. In some aspects, the amount sufficient of the ferulic acid is from 0.03 to 10% of the composition. In some aspects, the amount sufficient of the ferulic acid is from 0.04 to 10% of the composition. In some aspects, the amount sufficient of the ferulic acid is from 0.05 to 10% of the composition. In some aspects, the amount sufficient of the ferulic acid is from 0.06 to 10% of the composition. In some aspects, the amount sufficient of the ferulic acid is from 0.07 to 10% of the composition. In some aspects, the amount sufficient of the ferulic acid is from 0.08 to 10% of the composition. In some aspects, the amount sufficient of the ferulic acid is from 0.09 to 10% of the composition. In some aspects, the amount sufficient of the ferulic acid is from 0.1 to 10% of the composition. In some aspects, the amount sufficient of the ferulic acid is from 0.2 to 10% of the composition. In some aspects, the amount sufficient of the ferulic acid is from 0.3 to 10% of the composition. In some aspects, the amount sufficient of the ferulic acid is from 0.4 to 10% of the composition. In some aspects, the amount sufficient of the ferulic acid is from 0.5 to 10% of the composition. In some aspects, the amount sufficient of the ferulic acid is from 0.6 to 10% of the composition. In some aspects, the amount sufficient of the ferulic acid is from 0.7 to 10% of the composition. In some aspects, the amount sufficient of the ferulic acid is from 0.8 to 10% of the composition. In some aspects, the amount sufficient of the ferulic acid is from 0.9 to 10% of the composition. In some aspects, the amount sufficient of the ferulic acid is from 1 to 10% of the composition. In some aspects, the amount sufficient of the ferulic acid is from 2 to 10% of the composition. In some aspects, the amount sufficient of the ferulic acid is from 3 to 10% of the composition. In some aspects, the amount sufficient of the ferulic acid is from 4 to 10% of the composition. In some aspects, the amount sufficient of the ferulic acid is from 5 to 10% of the composition. In some aspects, the amount sufficient of the ferulic acid is from 6 to 10% of the composition. In some aspects, the amount sufficient of the ferulic acid is from 7 to 10% of the composition. In some aspects, the amount sufficient of the ferulic acid is from 8 to 10% of the composition. In some aspects, the amount sufficient of the ferulic acid is from 9 to 10% of the composition.

In some aspects, the at least one potentiating agent is cyclohexanecarboxylic acid. In some aspects, the amount sufficient of the cyclohexanecarboxylic acid is from 0.00001 to 10% of the composition. In some aspects, the amount sufficient of the cyclohexanecarboxylic acid is from 0.005 to 0.5% of the composition. In some aspects, the amount sufficient of the cyclohexanecarboxylic acid is from 0.0005 to 0.1% of the composition.

In some aspects, the amount sufficient of the cyclohexanecarboxylic acid is from 0.00002 to 10% of the composition. In some aspects, the amount sufficient of the cyclohexanecarboxylic acid is from 0.00004 to 10% of the composition. In some aspects, the amount sufficient of the cyclohexanecarboxylic acid is from 0.00006 to 10% of the composition. In some aspects, the amount sufficient of the cyclohexanecarboxylic acid is from 0.00008 to 10% of the composition. In some aspects, the amount sufficient of the cyclohexanecarboxylic acid is from 0.0001 to 10% of the composition. In some aspects, the amount sufficient of the cyclohexanecarboxylic acid is from 0.0002 to 10% of the composition. In some aspects, the amount sufficient of the cyclohexanecarboxylic acid is from 0.0004 to 10% of the composition. In some aspects, the amount sufficient of the cyclohexanecarboxylic acid is from 0.0006 to 10% of the composition. In some aspects, the amount sufficient of the cyclohexanecarboxylic acid is from 0.0008 to 10% of the composition. In some aspects, the amount sufficient of the cyclohexanecarboxylic acid is from 0.001 to 10% of the composition. In some aspects, the amount sufficient of the cyclohexanecarboxylic acid is from 0.002 to 10% of the composition. In some aspects, the amount sufficient of the cyclohexanecarboxylic acid is from 0.003 to 10% of the composition. In some aspects, the amount sufficient of the cyclohexanecarboxylic acid is from 0.004 to 10% of the composition.

In some aspects, the amount sufficient of the cyclohexanecarboxylic acid is from 0.005 to 10% of the composition. In some aspects, the amount sufficient of the cyclohexanecarboxylic acid is from 0.006 to 10% of the composition. In some aspects, the amount sufficient of the cyclohexanecarboxylic acid is from 0.007 to 10% of the composition. In some aspects, the amount sufficient of the cyclohexanecarboxylic acid is from 0.008 to 10% of the composition. In some aspects, the amount sufficient of the cyclohexanecarboxylic acid is from 0.009 to 10% of the composition. In some aspects, the amount sufficient of the cyclohexanecarboxylic acid is from 0.01 to 10% of the composition. In some aspects, the amount sufficient of the cyclohexanecarboxylic acid is from 0.02 to 10% of the composition. In some aspects, the amount sufficient of the cyclohexanecarboxylic acid is from 0.03 to 10% of the composition. In some aspects, the amount sufficient of the cyclohexanecarboxylic acid is from 0.04 to 10% of the composition. In some aspects, the amount sufficient of the cyclohexanecarboxylic acid is from 0.05 to 10% of the composition. In some aspects, the amount sufficient of the cyclohexanecarboxylic acid is from 0.06 to 10% of the composition. In some aspects, the amount sufficient of the cyclohexanecarboxylic acid is from 0.07 to 10% of the composition. In some aspects, the amount sufficient of the cyclohexanecarboxylic acid is from 0.08 to 10% of the composition. In some aspects, the amount sufficient of the cyclohexanecarboxylic acid is from 0.09 to 10% of the composition. In some aspects, the amount sufficient of the cyclohexanecarboxylic acid is from 0.1 to 10% of the composition. In some aspects, the amount sufficient of the cyclohexanecarboxylic acid is from 0.2 to 10% of the composition. In some aspects, the amount sufficient of the cyclohexanecarboxylic acid is from 0.3 to 10% of the composition. In some aspects, the amount sufficient of the cyclohexanecarboxylic acid is from 0.4 to 10% of the composition. In some aspects, the amount sufficient of the cyclohexanecarboxylic acid is from 0.5 to 10% of the composition. In some aspects, the amount sufficient of the cyclohexanecarboxylic acid is from 0.6 to 10% of the composition. In some aspects, the amount sufficient of the cyclohexanecarboxylic acid is from 0.7 to 10% of the composition. In some aspects, the amount sufficient of the cyclohexanecarboxylic acid is from 0.8 to 10% of the composition. In some aspects, the amount sufficient of the cyclohexanecarboxylic acid is from 0.9 to 10% of the composition. In some aspects, the amount sufficient of the cyclohexanecarboxylic acid is from 1 to 10% of the composition. In some aspects, the amount sufficient of the cyclohexanecarboxylic acid is from 2 to 10% of the composition. In some aspects, the amount sufficient of the cyclohexanecarboxylic acid is from 3 to 10% of the composition. In some aspects, the amount sufficient of the cyclohexanecarboxylic acid is from 4 to 10% of the composition. In some aspects, the amount sufficient of the cyclohexanecarboxylic acid is from 5 to 10% of the composition. In some aspects, the amount sufficient of the cyclohexanecarboxylic acid is from 6 to 10% of the composition. In some aspects, the amount sufficient of the cyclohexanecarboxylic acid is from 7 to 10% of the composition. In some aspects, the amount sufficient of the cyclohexanecarboxylic acid is from 8 to 10% of the composition. In some aspects, the amount sufficient of the cyclohexanecarboxylic acid is from 9 to 10% of the composition.

In some aspects, the at least one potentiating agent is mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.00001 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.005 to 0.5% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.001 to 0.2% of the composition.

In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.00002 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.00004 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.00006 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.00008 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.0001 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.0002 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.0004 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.0006 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.0008 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.001 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.002 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.003 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.004 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.005 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.006 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.007 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.008 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.009 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.01 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.02 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.03 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.04 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.05 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.06 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.07 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.08 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.09 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.1 to 10% of the composition. In some aspects, the amount sufficient of the mixture comprising (+−)-4-[(3,3-dimethyl-2-oxiranyl)

methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.2 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.3 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.4 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.5 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.6 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.7 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.8 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 0.9 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 1 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 2 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 3 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 4 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 5 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 6 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 7 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 8 to 10% of the composition. In some aspects, the amount sufficient of the mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[is from 9 to 10% of the composition.

In some aspects, the at least one potentiating agent is at least one polymethoxyflavonoid. In some aspects, the at least one polymethoxy flavonoid may be extracted from a botanical source. The extraction may be by any method readily selected by one of ordinary skill in the art. Non-limiting examples of extraction methods include the methods disclosed in Japanese Patent Application Publication No. JP 2009067755A, and Japanese Patent Application Publication No. JP 2011153084A.

In some aspects, the extract comprises a mixture of polymethoxyflavonoids. In some aspects the mixture comprises the following compounds:

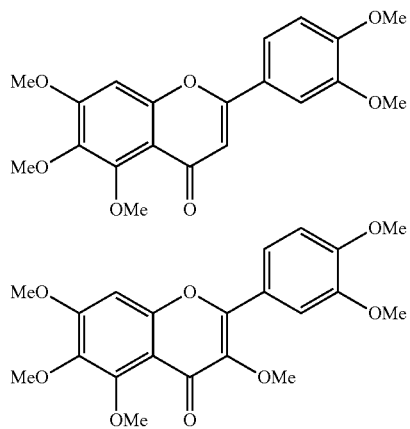

In some aspects, the amount sufficient of the at least one polymethoxyflavonoid is from 0.00001 to 10% of the composition. In some aspects, the amount sufficient of the at least one polymethoxyflavonoid is from 0.005 to 0.5% of the composition. In some aspects, the amount sufficient of the at least one polymethoxyflavonoid is from 0.001 to 0.2% of the composition.

In some aspects, the amount sufficient of the at least one polymethoxyflavonoid is from 0.00002 to 10% of the composition. In some aspects, the amount sufficient of the at least one polymethoxyflavonoid is from 0.00004 to 10% of the composition. In some aspects, the amount sufficient of the at least one polymethoxyflavonoid is from 0.00006 to 10% of the composition. In some aspects, the amount sufficient of the at least one polymethoxyflavonoid is from 0.00008 to 10% of the composition. In some aspects, the amount sufficient of the at least one polymethoxyflavonoid is from 0.0001 to 10% of the composition. In some aspects, the amount sufficient of the at least one polymethoxyflavonoid is from 0.0002 to 10% of the composition. In some aspects, the amount sufficient of the at least one polymethoxyflavonoid is from 0.0004 to 10% of the composition. In some aspects, the amount sufficient of the at least one polymethoxyflavonoid is from 0.0006 to 10% of the composition. In some aspects, the amount sufficient of the at least one polymethoxyflavonoid is from 0.0008 to 10% of the composition. In some aspects, the amount sufficient of the at least one polymethoxyflavonoid is from 0.001 to 10% of the composition. In some aspects, the amount sufficient of the at least one polymethoxyflavonoid is from 0.002 to 10% of the composition. In some aspects, the amount sufficient of the at least one polymethoxyflavonoid is from 0.003 to 10% of the composition. In some aspects, the amount sufficient of the at least one polymethoxyflavonoid is from 0.004 to 10% of the composition. In some aspects, the amount sufficient of the at least one polymethoxyflavonoid is from 0.005 to 10% of the composition. In some aspects, the amount sufficient of the at least one polymethoxyflavonoid is from 0.006 to 10% of the composition. In some aspects, the amount sufficient of the at least one polymethoxyflavonoid is from 0.007 to 10% of the composition. In some aspects, the amount sufficient of the at least one polymethoxyflavonoid is from 0.008 to 10% of the composition. In some aspects, the amount sufficient of the at least one polymethoxyflavonoid is from 0.009 to 10% of the composition. In some aspects, the amount sufficient of the at least one polymethoxyflavonoid is from 0.01 to 10% of the composition. In some aspects, the amount sufficient of the at least one polymethoxyflavonoid is from 0.02 to 10% of the composition. In some aspects, the amount sufficient of the at least one polymethoxyflavonoid is from 0.03 to 10% of the composition. In some aspects, the amount sufficient of the at least one polymethoxyflavonoid is from 0.04 to 10% of the composition. In some aspects, the amount sufficient of the at least one polymethoxyflavonoid is from 0.05 to 10% of the composition. In some aspects, the amount sufficient of the at least one polymethoxyflavonoid is from 0.06 to 10% of the composition. In some aspects, the amount sufficient of the at least one polymethoxyflavonoid is from 0.07 to 10% of the composition. In some aspects, the amount sufficient of the at least one polymethoxyflavonoid is from 0.08 to 10% of the composition. In some aspects, the amount sufficient of the at least one polymethoxyflavonoid is from 0.09 to 10% of the composition. In some aspects, the amount sufficient of the at least one polymethoxyflavonoid is from 0.1 to 10% of the composition. In some aspects, the amount sufficient of the at least one polymethoxyflavonoid is from 0.2 to 10% of the composition. In some aspects, the amount sufficient of the at least one polymethoxyflavonoid is from 0.3 to 10% of the composition. In some aspects, the amount sufficient of the at least one polymethoxyflavonoid is from 0.4 to 10% of the composition. In some aspects, the amount sufficient of the at least one polymethoxyflavonoid is from 0.5 to 10% of the composition. In some aspects, the amount sufficient of the at least one polymethoxyflavonoid is from 0.6 to 10% of the composition. In some aspects, the amount sufficient of the at least one polymethoxyflavonoid is from 0.7 to 10% of the composition. In some aspects, the amount sufficient of the at least one polymethoxyflavonoid is from 0.8 to 10% of the composition. In some aspects, the amount sufficient of the at least one polymethoxyflavonoid is from 0.9 to 10% of the composition. In some aspects, the amount sufficient of the at least one polymethoxyflavonoid is from 1 to 10% of the composition. In some aspects, the amount sufficient of the at least one polymethoxyflavonoid is from 2 to 10% of the composition. In some aspects, the amount sufficient of the at least one polymethoxyflavonoid is from 3 to 10% of the composition. In some aspects, the amount sufficient of the at least one polymethoxyflavonoid is from 4 to 10% of the composition. In some aspects, the amount sufficient of the at least one polymethoxyflavonoid is from 5 to 10% of the composition. In some aspects, the amount sufficient of the at least one polymethoxyflavonoid is from 6 to 10% of the composition. In some aspects, the amount sufficient of the at least one polymethoxyflavonoid is from 7 to 10% of the composition. In some aspects, the amount sufficient of the at least one polymethoxyflavonoid is from 8 to 10% of the composition. In some aspects, the amount sufficient of the at least one polymethoxyflavonoid is from 9 to 10% of the composition. In some aspects, the at least one potentiating agent is 3-(1-((3,5-dimethylisoxazol-4-yl)methyl)-1H-pyrazol-4-yl)-1-(3-hydroxybenzyl)imidazolidine-2,4-dione. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.00001 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.005 to 0.5% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.001 to 0.2% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.00001 to 0.005% of the composition.

In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.00002 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.00004 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.00006 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.00008 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.0001 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.0002 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.0004 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.0006 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.0008 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.001 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.002 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.003 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.004 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.005 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.006 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.007 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.008 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.009 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.01 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.02 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.03 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.04 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.05 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.06 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.07 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.08 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.09 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.1 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.2 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.3 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.4 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.5 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.6 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.7 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.8 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 0.9 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 1 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 2 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 3 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 4 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 5 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 6 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 7 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 8 to 10% of the composition. In some aspects, the amount sufficient of the 3-(1-((3,5-dimethylisoxazol-4-yl)methyl)-1H-pyrazol-4-yl)-1-(3-hydroxybenzyl)imidazolidine-2,4-dione is from 9 to 10% of the composition.

Some aspects presented herein provide a flavored article comprising
  a) the composition according to some aspects presented herein; and
  b) an orally acceptable carrier.

In some aspects, the flavored article is an oral care composition. As used herein, the term "oral care composition" refers to a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthwash, mousse, foam, mouthspray, lozenge, chewable tablet, chewing gum or denture product. The oral care composition may also be incorporated onto strips or films for direct application or attachment to oral surfaces.

As used herein, the term "dentifrice" includes paste, gel, or liquid formulations unless otherwise specified. The dentifrice composition may be a single phase composition or may be a combination of two or more separate dentifrice compositions. The dentifrice composition may be in any desired form, such as deep striped, surface striped, multi-layered, having a gel surrounding a paste, or any combination thereof. Each dentifrice composition in a dentifrice comprising two or more separate dentifrice compositions may be contained in a physically separated compartment of a dispenser and dispensed side-by-side.

As used herein, the term "dispenser" refers to any pump, tube, or container suitable for dispensing compositions such as dentifrices.

As used herein, the term "orally acceptable carrier or excipients" includes safe and effective materials and conventional additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

Cooling Compounds

Cooling compounds or compounds that have a physiological cooling effect on oral surfaces are common ingredients in a wide variety of products including edible compositions and personal care products and in flavor or perfume compositions for use in such products. Examples of edible compositions include confectionery, candies, chocolate, chewing gum, beverages and oral medicines. A class of topically applied compositions to which the present disclosure relates is for oral and throat care, which include products in powder, paste or liquid forms and which on being used are retained for a time sufficient to contact the surface and the internal mucous membrane of the oral cavities or the pharynx. Such products include for example, mouthwashes, dental and throat lozenges, gargles, chewing gum, dentifrice or toothpastes, toothpicks, dental tablets and powders and topical solutions for application in dental treatment, as well as cough-syrups, chewable antacids and digestion promoting preparations.

The pleasant cooling sensation provided by cooling compounds contributes to the appeal and acceptability of the products. In particular, oral care products such as dentifrices and mouthwashes are formulated with coolants because they provide breath freshening effects and a clean, cool, fresh feeling in the mouth.

Without intending to be limited to any particular theory, sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, one candidate involved in sensing cold has been identified and designated as cold- and menthol-sensitive receptor (CMR1) or TRPM8.

The TRPM8 nomenclature for the receptor comes from its characterization as a non-selective cation channel of the transient receptor potential (TRP) family that is activated by stimuli including low temperatures, menthol and other chemical coolants. However, the precise mechanisms underlying the perception of a pleasant cooling sensation on skin or oral surfaces are presently not clearly understood.

Without intending to be limited to any particular theory, while it has been demonstrated that the TRPM8 receptor is activated by menthol and other coolants, it is not fully understood what other receptors may be involved and to what extent these receptors need to be stimulated or perhaps suppressed in order that the overall perceived sensation would be pleasant, cooling and refreshing. For example, menthol is widely used as a cooling agent, but menthol can also produce other sensations including tingling, burning, prickling and stinging as well as a minty smell and bitter taste. Thus, it can be inferred that menthol, and other cooling agents may act on many different receptors, including cold, warm, pain and taste receptors.

However, it is not readily discernible how to isolate which receptor activities would result in a specific sensation such as pleasant cooling without the undesirable sensations such as bitterness or irritation. Neither is it apparent how to control the activity of coolants or other sensory agents such that only the desired sensation is elicited from use of a particular sensory agent. The present disclosure is thus based on the discovery of agents that can be used to enhance and/or modulate the activity of cooling and flavoring compounds.

In some aspects, the at least one cooling compound is selected from the group consisting of: menthol, menthone, isopulegol, N-ethyl p-menthanecarboxamide (WS-3), N,2,3-trimethyl-2-isopropylbutanamide (WS-23), ethyl N-[[5-methyl-2-(isopropyl)cyclohexyl]carbonyl]glycinate, menthyl lactate, menthone glycerine acetal (Frescolat® MGA), mono-menthyl succinate (Physcool®), mono-menthyl glutarate, 0-menthyl glycerine (CoolAct® 10) and 2-sec-butyl-cyclohexanone (Freskomenthe®), menthane, camphor, pulegol, cineol, mint oil, peppermint oil, spearmint oil, eucalyptus oil, 3-1-menthoxypropane-1,2-diol, 3-1-menthoxy-2-methylpropane-1,2-diol, p-menthane-3,8-diol, 2-1-menthoxyethane-1-ol, 3-1-menthoxypropane-1-ol, and 4-1-menthoxybutane-1-ol.

In some aspects, the at least one cooling compound is selected from the cooling compounds disclosed in European Patent EP2346475 B1.

In some aspects, the at least one cooling compound is selected from the cooling compounds disclosed in U.S. Pat. No. 9,718,839 B2.

Potentiation of the Flavor, Cooling and Refreshing Intensity Provided by the At Least One Cooling Compound The present disclosure describes the potentiation of the flavor and cooling intensity of the at least one cooling compound by certain compounds (also referred to herein as potentiation agents).

The potentiation may be determined by any method readily selected by one of ordinary skill in the art. In some aspects, the potentiation is determined using a sensory panel. In the aspects where the potentiation is determined using a sensory panel a subject may contact their oral cavity with a composition, and rate the perceived flavor strength and cooing strength of the composition.

In some aspects, the sensory panel may be performed according to the methods described in M. C. Meilgaard, et al., Sensory Evaluation Techniques, 4th Ed. (2007).

In some aspects, the perceived flavor intensity may be rated from 0 to 5, wherein 0 is no perceived flavor intensity, 1 is a very low perceived flavor intensity, 2 is a low perceived flavor intensity, 3 is a moderate perceived flavor intensity, 4 is a high perceived flavor intensity, and 5 is a very high perceived flavor intensity.

In some aspects, compositions lacking the at least one potentiating agent have a perceived flavor intensity of 3, and the addition of the at least one potentiating agent increases the perceived flavor intensity.

In some aspects, the perceived cooling intensity may be rated from 0 to 5, wherein 0 is no perceived cooling intensity, 1 is a very low perceived cooling intensity, 2 is a low perceived cooling intensity, 3 is a moderate perceived cooling intensity, 4 is a high perceived cooling intensity, and 5 is a very high perceived flavor intensity.

In some aspects, compositions lacking the at least one potentiating agent have a perceived cooling intensity of 3, and the addition of the at least one potentiating agent increases the perceived cooling intensity.

In some aspects, the at least one potentiation agent is selected from the group consisting of: methyl acetate, (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[, polymethoxy flavonoid, 3-(1-((3,5-dimethylisoxazol-4-yl)methyl)-1H-pyrazol-4-yl)-1-(3-hydroxybenzyl)imidazolidine-2,4-dione, and combinations thereof.

In some aspects, the composition comprises:
a) at least one cooling compound;
b) a mixture comprising methyl acetate and at least one other potentiating agent selected from the group consisting of: (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, a mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[3,2-g]chromen-7-one, at least one polymethoxy flavonoid, 3-(1-((3,5-dimethylisoxazol-4-yl)methyl)-1H-pyrazol-4-yl)-1-(3-hydroxybenzyl)imidazolidine-2,4-dione, and combinations thereof,
wherein the mixture is present in the composition in an amount sufficient to increase the intensity of flavor of the at least one cooling compound and increase the intensity of the cooling sensation of the at least one cooling compound, when a subject is contacted with the composition.

In some aspects the ratio of the methyl acetate to the at least one other potentiating agent in the mixture is from 1:0.00001 to 1:10.

In some aspects the ratio of the methyl acetate to the at least one other potentiating agent in the mixture is from 1:0.0001 to 1:1.

In some aspects the ratio of the methyl acetate to the at least one other potentiating agent in the mixture is from 1:0.005 to 1:0.1.

In some aspects, the mixture comprises methyl acetate and 3-(1-((3,5-dimethylisoxazol-4-yl)methyl)-1H-pyrazol-4-yl)-1-(3-hydroxybenzyl)imidazolidine-2,4-dione.

In some aspects, the amount sufficient of the mixture is from 0.02 to 10,000 ppm.

In some aspects, the amount sufficient of the mixture is from 1 to 10,000 ppm.

In some aspects, the amount sufficient of the mixture is from 50 to 5,000 ppm.

In some aspects, the amount sufficient of the mixture is from 100 to 2,000 ppm.

In some aspects, the amount sufficient of the mixture is from 0.1 to 1,000 ppm.

In some aspects, the amount sufficient of the mixture is from 0.02 to 100 ppm.

In some aspects, the amount sufficient of the mixture is from 0.2 to 20 ppm.

In some aspects, the amount sufficient of the mixture is from 0.02 to 10,000 ppm.

In some aspects, the amount sufficient of the mixture is from 0.04 to 10,000 ppm. In some aspects, the amount sufficient of the mixture is from 0.06 to 10,000 ppm. In some aspects, the amount sufficient of the mixture is from 0.08 to 10,000 ppm. In some aspects, the amount sufficient of the mixture is from 0.1 to 10,000 ppm. In some aspects, the amount sufficient of the mixture is from 0.2 to 10,000 ppm. In some aspects, the amount sufficient of the mixture is from 0.3 to 10,000 ppm. In some aspects, the amount sufficient of the mixture is from 0.4 to 10,000 ppm. In some aspects, the amount sufficient of the mixture is from 0.5 to 10,000 ppm. In some aspects, the amount sufficient of the mixture is from 0.6 to 10,000 ppm. In some aspects, the amount sufficient of the mixture is from 0.7 to 10,000 ppm. In some aspects, the amount sufficient of the mixture is from 0.8 to 10,000 ppm. In some aspects, the amount sufficient of the mixture is from 0.9 to 10,000 ppm. In some aspects, the amount sufficient of the mixture is from 1 to 10,000 ppm. In some aspects, the amount sufficient of the mixture is from 2 to 10,000 ppm. In some aspects, the amount sufficient of the mixture is from 3 to 10,000 ppm. In some aspects, the amount sufficient of the mixture is from 4 to 10,000 ppm. In some aspects, the amount sufficient of the mixture is from 5 to 10,000 ppm. In some aspects, the amount sufficient of the mixture is from 6 to 10,000 ppm. In some aspects, the amount sufficient of the mixture is from 7 to 10,000 ppm. In some aspects, the amount sufficient of the mixture is from 8 to 10,000 ppm. In some aspects, the amount sufficient of the mixture is from 9 to 10,000 ppm. In some aspects, the amount sufficient of the mixture is from 10 to 10,000 ppm. In some aspects, the amount sufficient of the mixture is from 20 to 10,000 ppm. In some aspects, the amount sufficient of the mixture is from 30 to 10,000 ppm. In some aspects, the amount sufficient of the mixture is from 40 to 10,000 ppm. In some aspects, the amount sufficient of the mixture is from 50 to 10,000 ppm. In some aspects, the amount sufficient of the mixture is from 60 to 10,000 ppm. In some aspects, the amount sufficient of the mixture is from 70 to 10,000 ppm. In some aspects, the amount sufficient of the mixture is from 80 to 10,000 ppm. In some aspects, the amount sufficient of the mixture is from 90 to 10,000 ppm. In some aspects, the amount sufficient of the mixture is from 100 to 10,000 ppm. In some aspects, the amount sufficient of the mixture is from 200 to 10,000 ppm. In some aspects, the amount sufficient of the mixture is from 300 to 10,000 ppm. In some aspects, the amount sufficient of the mixture is from 400 to 10,000 ppm. In some aspects, the amount sufficient of the mixture is from 500 to 10,000 ppm. In some aspects, the amount sufficient of the mixture is from 600 to 10,000 ppm. In some aspects, the amount sufficient of the mixture is from 700 to 10,000 ppm. In some aspects, the amount sufficient of the mixture is from 800 to 10,000 ppm. In some aspects, the amount sufficient of the mixture is from 900 to 10,000 ppm. In some aspects, the amount sufficient of the mixture is from 1,000 to 10,000 ppm. In some aspects, the amount sufficient of the mixture is from 2,000 to 10,000 ppm. In some aspects, the amount sufficient of the mixture is from 3,000 to 10,000 ppm. In some aspects, the amount sufficient of the mixture is from 4,000 to 10,000 ppm. In some aspects, the amount sufficient of the mixture is from 5,000 to 10,000 ppm. In some aspects, the amount sufficient of the mixture is from 6,000 to 10,000 ppm. In some aspects, the amount sufficient of the mixture is from 7,000 to 10,000 ppm. In some aspects, the amount sufficient of the mixture is from 8,000 to 10,000 ppm. In some aspects, the amount sufficient of the mixture is from 9,000 to 10,000 ppm.

In some aspects, the amount sufficient of the mixture is 0.02, or 0.04, or 0.06, or 0.08, or 0.10, or 0.20, or 0.30, or 0.40, or 0.50, or 0.60, or 0.70, or 0.80, or 0.90, or 1, or 2, or 3, or 4, or 5, or 6, or 7, or 8, or 9, or 10, or 20, or 30, or 40, or 50, or 60, or 70, or 80, or 90, or 100, or 200, or 300, or 400, or 500, or 600, or 700, or 800, or 900, or 1,000, or 2,000, or 3,000, or 4,000, or 5,000, or 6,000, or 7,000, or 8,000, or 9,000, or 10,000 ppm.

In some aspects, the cyclohexanecarboxylic acid is a chlorogenic acid. As used herein, the term "chlorogenic acid" refers to phenolic acids found in plant materials.

Chlorogenic acids may be classified by the identity, number, and position of the acyl residues on the quinic acid.

The cyclohexanecarboxylic acids of the present invention can be obtained commercially, synthesized according to procedures known in the art, for example, as described by Sefkow (Eur. J. Org. Chem. 2001, 1137-1141) or obtained from a variety of botanicals such as fruits (for example, apples, apricots, blackberries, blueberries, cherries, citrus fruits, peaches, pears, plums and strawberries), plant leaves (for example, blueberry. mate and eucommia leaves), vegetables (for example, artichokes, Brussels sprouts, cabbages, carrots, eggplants, kales, peppers, potatoes and tomatoes) and other plants (for example, bamboos, coffee beans, honeysuckle flowers, sunflower seeds and yerba mate).

In some aspects, the cyclohexanecarboxylic acid is selected from the cyclohexanecarboxylic acids disclosed in International Patent Application Publication No. WO 2002/100192 A1.

In some aspects, the cyclohexanecarboxylic acid is selected from the cyclohexanecarboxylic acids disclosed in International Patent Application Publication No. WO 2016/209664 A1.

In some aspects, the cyclohexanecarboxylic acid is selected from the cyclohexanecarboxylic acids disclosed in U.S. Pat. No. 6,632,459 B2.

In some aspects, the cyclohexanecarboxylic acid is selected from the group consisting of (1S,3R,4R,5R)-3-[[3-(3,4-dihydroxyphenyl)-1-oxo-2-propen-1-yl]oxy]-1,4,5-trihydroxy-cyclohexanecarboxylic acid, (1R,3R,4S,5R)-3-[[(2E)-3-(3,4-dihydroxyphenyl)-1-oxo-2-propen-1-yl]oxy]-1,4,5-trihydroxy-cyclohexanecarboxylic acid, (1α,3R,4α,5R)-4-[[3-(3,4-dihydroxyphenyl)-1-oxo-2-propen-1-yl]oxy]-1,3,5-trihydroxy-cyclohexanecarboxylic acid, (1S,3R,4R,5R)-3,4-bis[[3-(3,4-dihydroxyphenyl)-1-oxo-2-propenyl]oxy]-1,5-dihydroxy-cyclohexanecarboxylic acid, (1α,3R,4α,5R)-3,5-bis[[3-(3,4-dihydroxyphenyl)-1-oxo-2-propen-1-yl]oxy]-1,4-dihydroxy-cyclohexanecarboxylic acid, and (1R,3R,4S,5R)-3,4-bis[[3-(3,4-dihydroxyphenyl)-1-oxo-2-propen-1-yl]oxy]-1,5-dihydroxy-cyclohexanecarboxylic acid.

In some aspects, the cyclohexanecarboxylic acid is (1R,3R,4S,5R)-3-[[(2E)-3-(3,4-dihydroxyphenyl)-1-oxo-2-propen-1-yl]oxy]-1,4,5-trihydroxy-cyclohexanecarboxylic acid.

In some aspects, the cyclohexanecarboxylic acid is purified from green coffee.

Examples of methods to purify cyclohexanecarboxylic acid from green coffee, and compositions comprising cyclohexanecarboxylic acid extracted from green coffee are disclosed in Del Rio et al., Nutrients 2(8): 820-833 (2010).

In some aspects, the cyclohexanecarboxylic acid is selected from the group consisting of 5-caffeoylquinic acid (5-CQA), 3-caffeoylquinic acid (3-CQA), 4-caffeoylquinic acid (4-CQA), 3,4-dicaffeoylquinic acid (3,4-diCQA), 3,5-dicaffeoylquinic acid (3,5-diCQA), 4,5-dicaffeoylquinic acid (4,5-diCQA), 3-feruloylquinic acid (3-FQA), 4-feruloylquinic acid (4-FQA), 5-feruloylquinic acid (5-FQA), 3-p-coumaroylquinic acid (3-p-CoQA), 4-p-coumaroylquinic acid (4-p-CoQA), 5-p-coumaroylquinic acid (3-p-CoQA), 3,4-caffeoylferuloylquinic acid (3,4-CFQA), 3,4-feruloylqcaffeoylquinic acid (3,4-FCQA), 3,5-caffeoylferuloylquinic acid (3,5-CFQA), 3,5-feruloylqcaffeoylquinic acid (3,4-FCQA), 4,5-caffeoylferuloylquinic acid (4,5-CFQA), 4,5-feruloylqcaffeoylquinic acid (4,5-FCQA), and combinations thereof.

Flavor Systems

In some aspects, the composition further comprises a flavor system. The flavor system may mask any unpleasant taste and sensations due to certain components of the composition such as antimicrobial actives or peroxide. Without intending to be limited to any particular theory, pleasant tasting compositions improve user compliance to prescribed or recommended use of oral care products. The present flavor system may also comprise traditional flavor components, in particular those that are relatively stable in the presence of usual oral care product carrier materials or excipients. The combination of the selected flavoring system with the compositions presented herein may provide a high-impact refreshing sensation with a well-rounded flavor profile.

In some aspects, the flavor system may comprise additional flavor ingredients including but not limited to peppermint oil, corn mint oil, spearmint oil, oil of wintergreen, clove bud oil, cassia, sage, parsley oil, marjoram, lemon, lime, orange, cis-jasmone, 2,5-dimethyl-4-hydroxy-3(2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, 0-damascenone, ionone, gamma decalactone, gamma nonalactone, gamma undecalactone and mixtures thereof.

Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be supplied in the composition as single or purified chemicals or by addition of natural oils or extracts that have preferably undergone a refining treatment to remove components that are relatively unstable and may degrade and alter the desired flavor profile, resulting in a less acceptable product from an organoleptic standpoint. Flavoring agents may generally be used in the compositions at levels of from about 0.001% to about 5%, by weight of the composition.

In some aspects, the flavor system may further include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-di-hydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used.

In some aspects, the composition may contains from about 0.1% to about 10% of sweetener, alternatively from about 0.1% to about 1%, by weight of the composition.

In some aspects, the flavor system may further include salivating agents, warming agents, and numbing agents. These agents may be present in the compositions at a level of from about 0.001% to about 10%, alternatively from about 0.1% to about 1%, by weight of the composition.

Suitable salivating agents include Jambu® manufactured by Takasago. Suitable numbing agents include benzocaine, lidocaine, clove bud oil, and ethanol. Examples of warming agents include ethanol, capsicum and nicotinate esters, such as benzyl nicotinate.

In addition to the components described above, the present compositions may comprise additional optional components collectively referred to as orally acceptable carrier materials.

Orally Acceptable Carrier Materials and Products

In some aspects, the orally acceptable carrier may comprise one or more compatible solid or liquid excipients or diluents which are suitable for topical oral administration. By "compatible," as used herein, is meant that the components of the composition are capable of being commingled without interaction in a manner which would substantially reduce stability and/or efficacy.

The carriers or excipients of the present disclosure can include the usual and conventional components of dentifrices, non-abrasive gels, subgingival gels, mouthwashes or rinses, mouth sprays, chewing gums, lozenges and breath mints.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S.

Pat. Nos. 5,213,790; 5,145,666 and 5,281,410 all to Lukacovic et al., and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910 both to Damani. Carriers suitable for the preparation of compositions of the present disclosure are well known in the art. Their selection will depend on secondary considerations like taste, cost, and shelf stability, and the like.

Tables 1 to 5 below describe oral care products suitable for use with a composition according to the aspects described herein.

TABLE 1

An example of a paste dentifrice formulation

| Ingredients | Amount (% wt) | Function |
|---|---|---|
| Polyethylene glycol 400 | 2.000 | humectant |
| Xanthan Gum | 0.600 | thickener |
| Sorbitol 70% Solution | 50.000 | humectant |
| Sodium Fluoride | 0.220 | Active ingredient |
| Sodium Benzoate | 0.200 | perservative |
| Water | 15.230 | solvent |
| Hydrated Silica (Tixosil 73) | 22.000 | abrasive |
| Hydrated Silica (Tixosil 43) | 7.000 | thickener |
| Titanium Dioxide CI77891 | 0.500 | opacifier |
| Sodium Lauryl Sulfate | 1.250 | surfactant |
| Flavor | 1.200 | Flavoring agent |
| Sodium saccharin | 0.25 | sweetener |

TABLE 2

An Example of a gel dentifrice formulation

| Ingredients | Amount (% wt) | Function |
|---|---|---|
| Xanthan Gum | 0.800% | thickener |
| Flavor | 1.200% | Flavoring agent |
| DI/Purified Water | Q.S to Final Wt. | solvent |
| Sodium Lauryl Sulfate | 1.500% | surfactant |
| Sodium Fluoride | 0.220% | Active ingredient |
| Sorbitol 70% Solution | 30.000% | humectant |
| Sodium Saccharin | 0.200% | sweetener |
| Glycerine | 5.000% | humectant |
| Sodium Benzoate | 0.200% | preservative |
| Sucralose | 0.050% | sweetener |
| Hydrated Silica (Tixosil 63) | 20.000% | abrasive |
| Hydrated Silica (Tixosil 43) | 5.000% | thickener |

TABLE 3

An example of a chalk base formulation

| Ingredients | Amount (% wt) | Function |
|---|---|---|
| water | | Solvent |
| sorbitol | 26 | Humectant |
| Methylparaben | 0.2 | Preservative |
| Xanthan Gum | 0.6 | Thickener |
| Polyethylene glycol 400 | 1.6 | humectant |
| Hydrated Silica | 10 | thickener |

TABLE 3-continued

An example of a chalk base formulation

| Ingredients | Amount (% wt) | Function |
|---|---|---|
| Calcium carbonate | 28 | Abrasive |
| Sodium Lauryl Sulfate | 1.25 | Surfactant |
| Flavor | 1 | Flavoring agent |
| Sodium Saccharin | 0.2 | sweetener |

TABLE 4

An example of Dicalcium phosphate Dihydrate toothpaste base

| Ingredients | Amount (% wt) | Function |
|---|---|---|
| Polyethylene glycol | 2 | Humectant |
| Binder | 1 | Thickener |
| Sorbitol 70% Syrup | 40 | Humectant |
| Glycerine | 10 | Thickener |
| Sodium Fluoride | 0.1 | Active ingredient |
| Sodium monofluorophosphate | 0.5 | Active ingredient |
| Methyl paraben | 0.1 | Preservative |
| Propyl paraben | 0.1 | Preservative |
| Dicalcium phosphate Dihydrate | 40 | Abrasive |
| Titanium Dioxide CI77891 | 0.5 | Opacifier |
| Sodium Lauryl Sulfate | 2 | Surfactant |
| Flavor | 1.2 | Flavoring agent |
| Sodium Saccharin | 0.2 | sweetener |
| water | 2.4 | Solvent |

TABLE 5

An example of an alcohol free mouthwash formulation

| Ingredients | Amount (% wt) | Function |
|---|---|---|
| Propylene Glycol | 10.000 | humectant |
| Flavor | 0.240 | Flavouring agent |
| DI/Purified Water | Q.S to Final Wt. | solvent |
| Poloxamer 407 NF | 0.240 | Co-solvent |
| Sodium Lauryl Sulfate | 0.040 | Surfactant |
| Sorbitol 70% Solution | 10.000 | humectant |
| Sodium Saccharin | 0.030 | sweetener |
| Glycerine | 3.000 | humectant |
| Sodium Benzoate | 0.100 | preservative |
| Sucralose | 0.020 | sweetener |
| Benzoic Acid | 0.050 | preservative |

TABLE 6

An example of alcohol containing mouthwash formulation

| Ingredients | Amount (% wt) | Function |
|---|---|---|
| Ethyl Alcohol 190 Proof | 21.000% | solubilizer |
| Flavor | 0.240% | Flavouring agent |
| DI/Purified Water | Q.S to Final Wt. | solvent |
| Poloxamer 407 NF | 0.240% | Co-solvent |
| Sodium Lauryl Sulfate | 0.040% | Surfactant |
| Sorbitol 70% Solution | 10.000% | humectant |
| Sodium Saccharin | 0.030% | sweetener |
| Glycerine | 3.000% | humectant |
| Sodium Benzoate | 0.100% | preservative |
| Sucralose | 0.020% | sweetener |
| Benzoic Acid | 0.050% | preservative |

Examples of suitable orally acceptable carriers and oral care products are disclosed in European Patent EP2346475 B1.

In some aspects, where the composition is formulated in an oral care product comprising a dentifrice, the effective amount of methyl acetate in the composition is 500 ppm.

In some aspects, where the composition is formulated in an oral care product comprising a mouthwash, the effective amount of methyl acetate in the composition is 100 ppm.

In some aspects, where the composition is formulated in an oral care product comprising a dentifrice, the effective amount of 3-(1-((3,5-dimethylisoxazol-4-yl)methyl)-1H-pyrazol-4-yl)-1-(3-hydroxybenzyl)imidazolidine-2,4-dione in the composition is 20 ppm.

In some aspects, where the composition is formulated in an oral care product comprising a mouthwash, the effective amount of 3-(1-((3,5-dimethylisoxazol-4-yl)methyl)-1H-pyrazol-4-yl)-1-(3-hydroxybenzyl)imidazolidine-2,4-dione in the composition is 2 ppm.

In some aspects, where the composition is formulated in an oral care product comprising a dentifrice, the effective amount of (+)-methyl(1R)-cis-3-oxo-2-pentyl-1-cyclopentaneacetate in the composition is 100 ppm.

In some aspects, where the composition is formulated in an oral care product comprising a mouthwash, the effective amount of (+)-methyl(1R)-cis-3-oxo-2-pentyl-1-cyclopentaneacetate in the composition is 1,000 ppm.

In some aspects, where the composition is formulated in an oral care product comprising a dentifrice, the effective amount of n-(1-propylbutyl)-1,3-benzodioxole-5-carboxamide in the composition is 20 ppm.

In some aspects, where the composition is formulated in an oral care product comprising a mouthwash, the effective amount of n-(1-propylbutyl)-1,3-benzodioxole-5-carboxamide in the composition is 5 ppm.

In some aspects, where the composition is formulated in an oral care product comprising a dentifrice, the effective amount of phoretin in the composition is 200 ppm.

In some aspects, where the composition is formulated in an oral care product comprising a mouthwash, the effective amount of phloretin in the composition is 20 ppm.

In some aspects, where the composition is formulated in an oral care product comprising a dentifrice, the effective amount of cyclohexanecarboxylic acid in the composition is 500 ppm.

In some aspects, where the composition is formulated in an oral care product comprising a mouthwash, the effective amount of cyclohexanecarboxylic acid in the composition is 50 ppm.

In some aspects, where the composition is formulated in an oral care product comprising a dentifrice, the effective amount of ferulic acid in the composition is 500 ppm.

In some aspects, where the composition is formulated in an oral care product comprising a mouthwash, the effective amount of ferulic acid in the composition is 50 ppm.

In some aspects, where the composition is formulated in an oral care product comprising a dentifrice, the effective amount of the at least one polymethoxy flavonoid in the composition is 50 ppm.

In some aspects, where the composition is formulated in an oral care product comprising a mouthwash, the effective amount of the at least one polymethoxy flavonoid in the composition is 5 ppm.

In some aspects, where the composition is formulated in an oral care product comprising a dentifrice, the effective amount of mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[in the composition is 50 ppm.

In some aspects, where the composition is formulated in an oral care product comprising a mouthwash, the effective amount of mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[in the composition is 5 ppm.

Methods

In some aspects, methods of use comprise contacting a subject's dental enamel surfaces and mucosa with the oral compositions described herein. The method of treatment may be by brushing with a dentifrice or rinsing with a dentifrice slurry or mouthwash. Other methods include contacting the topical oral gel, denture product, mouthspray, or other form with the subject's teeth and oral mucosa. The subject may be any person or animal whose oral cavity is contacted with the oral composition. By animal is meant to include household pets or other domestic animals, or animals kept in captivity.

Some aspects presented herein provide a method,
wherein the method provides a cooling sensation to a subject in need thereof,
wherein the method comprises contacting the subject with a composition according to some aspects presented herein,
wherein the method increases the intensity of the cooling effect of the at least one cooling compound perceived by the subject, compared to the intensity of the cooling effect perceived by a subject contacted with a composition lacking the at least one potentiating agent, and
wherein the method increases the intensity of the flavor of the at least one cooling compound perceived by the subject, compared to the intensity of the flavor of the at least one cooling compound perceived by a subject contacted with a composition lacking the at least one potentiating agent.

Some aspects presented herein provide a method,
wherein the method provides a cooling sensation to a subject in need thereof,
wherein the method comprises contacting the subject with a product according to some aspects presented herein,
wherein the method increases the intensity of the cooling effect of the at least one cooling compound perceived by the subject, compared to the intensity of the cooling effect perceived by a subject contacted with a product lacking the at least one potentiating agent, and
wherein the method increases the intensity of the flavor of the at least one cooling compound perceived by the subject, compared to the intensity of the flavor of the at least one cooling compound perceived by a subject contacted with a product lacking the at least one potentiating agent.

The present invention is best illustrated but is not limited to the following examples.

EXAMPLES

Example 1

Sensory Evaluation of Compositions According to Some Aspects Presented Herein

Table 7 below describes ten test formulations. Sample 1 was a control formulation, lacking a potentiating agent. Samples 2-10 contain the potentiating agents described.

TABLE 7

| Ingredients | Sample1 | Sample2 | Sample3 | Sample4 | Sample5 | Sample6 | Sample7 | Sample8 | Sample9 | Sample10 |
|---|---|---|---|---|---|---|---|---|---|---|
| Polyethylene glycol 400 | 2.00 | 2.00 | 2.00 | 2.00 | 2.00 | 2.00 | 2.00 | 2.00 | 2.00 | 2.00 |
| Xanthan Gum | 0.60 | 0.60 | 0.60 | 0.60 | 0.60 | 0.60 | 0.60 | 0.60 | 0.60 | 0.60 |
| Sorbitol 70% Solution | 50.00 | 50.00 | 50.00 | 50.00 | 50.00 | 50.00 | 50.00 | 50.00 | 50.00 | 50.00 |
| Sodium Fluoride | 0.22 | 0.22 | 0.22 | 0.22 | 0.22 | 0.22 | 0.22 | 0.22 | 0.22 | 0.22 |
| Sodium Benzoate | 0.20 | 0.20 | 0.20 | 0.20 | 0.20 | 0.20 | 0.20 | 0.20 | 0.20 | 0.20 |
| Water | 14.98 | 14.93 | 14.88 | 14.98 | 14.98 | 14.98 | 14.98 | 14.98 | 14.98 | 14.78 |
| Hydrated Silica (Tixosil 73) | 22.00 | 22.00 | 22.00 | 22.00 | 22.00 | 22.00 | 22.00 | 22.00 | 22.00 | 22.00 |
| Hydrated Silica (Tixosil 43) | 7.00 | 7.00 | 7.00 | 7.00 | 7.00 | 7.00 | 7.00 | 7.00 | 7.00 | 7.00 |
| Titanium Dioxide CI77891 | 0.50 | 0.50 | 0.50 | 0.50 | 0.50 | 0.50 | 0.50 | 0.50 | 0.50 | 0.50 |
| Sodium Lauryl Sulfate | 1.25 | 1.25 | 1.25 | 1.25 | 1.25 | 1.25 | 1.25 | 1.25 | 1.25 | 1.25 |
| Peppermint flavor 703414 03828T | 1.00 | 1.00 | 1.00 | 1.00 | 1.00 | 1.00 | 1.00 | 1.00 | 1.00 | 1.00 |
| Methyl acetate | 0.00 | 0.05 | 0.00 | 0.00 | 0.00 | 0.00 | 0.00 | 0.00 | 0.00 | 0.00 |
| (+)-methyl(1R)-cis-3-oxo-2-pentyl-1-cyclopentaneacetate | 0.00 | 0.00 | 0.10 | 0.00 | 0.00 | 0.00 | 0.00 | 0.00 | 0.00 | 0.00 |
| N-(1-propylbutyl)-1,3-benzodioxole-5-carboxamide | 0.00 | 0.00 | 0.00 | 0.002 | 0.00 | 0.00 | 0.00 | 0.00 | 0.00 | 0.00 |
| PHLORETIN NAT 980626 | 0.00 | 0.00 | 0.00 | 0.00 | 0.002 | 0.00 | 0.00 | 0.00 | 0.00 | 0.00 |
| Ferulic acid | 0.00 | 0.00 | 0.00 | 0.00 | 0.00 | 0.005 | 0.00 | 0.00 | 0.00 | 0.00 |
| Chlorogenic acid | 0.00 | 0.00 | 0.00 | 0.00 | 0.00 | 0.00 | 0.005 | 0.00 | 0.00 | 0.00 |
| Mixture comprising (+-)-4-[(3,3-dimethyl-2-oxiranyl)methoxy]-7H-furo[3,2-g]chromen-7-one, (+-)-4-(2,3-dihydroxy-3-methylbutoxy)-7H-furo[3,2-g]chromen-7-one, 5,7-dimethoxy-2H-chromen-2-one, and (+-)-9[(3,3-dimethyl-2-oxiranyl)methoxy]-4-methoxy-7H-furo[NAT 935922 | 0.00 | 0.00 | 0.00 | 0.00 | 0.00 | 0.00 | 0.00 | 0.0005 | 0.00 | 0.00 |
| PMF(polymethoxyflavonoid) | 0.00 | 0.00 | 0.00 | 0.00 | 0.00 | 0.00 | 0.00 | 0.00 | 0.0005 | 0.00 |
| 3-(1-((3,5-dimethylisoxazol-4-yl)methyl)-1H-pyrazol-4-yl)-1-(3-hydroxybenzyl)imidazolidine-2,4-dione 927893 0.1% in PG | 0.00 | 0.00 | 0.00 | 0.00 | 0.00 | 0.00 | 0.00 | 0.00 | 0.00 | 0.2 |
| Saccharin | 0.25 | 0.25 | 0.25 | 0.25 | 0.25 | 0.25 | 0.25 | 0.25 | 0.25 | 0.25 |

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 8.

TABLE 8

| | Sample 1 | Sample 2 | Sample 3 | Sample 4 | Sample 5 | Sample 6 | Sample 7 | Sample 8 | Sample 9 | Sample 10 |
|---|---|---|---|---|---|---|---|---|---|---|
| Flavor intensity | 3 | 5 | 5 | 4 | 5 | 4 | 4 | 4 | 4 | 5 |
| Cooling intensity | 3 | 4 | 5 | 5 | 5 | 4 | 4 | 4 | 4 | 5 |

These data suggest that potentiating agents selected from the group consisting of: methyl acetate, (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, a mixture comprising (+−)-4-[(3,3-dimethyl-2-oxiranyl)methoxy]-7H-furo[3,2-g]chromen-7-one, (+−)-4-(2,3-dihydroxy-3-methylbutoxy)-7H-furo[3,2-g]chromen-7-one, 5,7-dimethoxy-2H-chromen-2-one, and (+−)-9-[(3,3-dimethyl-2-oxiranyl)methoxy]-4-methoxy-7H-furo[, polymethoxy flavonoid, 3-(1-((3,5-dimethylisoxazol-4-yl)methyl)-1H-pyrazol-4-yl)-1-(3-hydroxybenzyl)imidazolidine-2,4-dione were able to increase both the perceived flavor intensity and the perceived cooling intensity of the mint flavor of test toothpaste formulation.

Example 2

Sensory Evaluation of Compositions According to Some Aspects Presented Herein

Table 9 below describes four test formulations. Sample 1 was a control formulation, lacking a potentiating agent. Samples 2-4 contain methyl acetate as the potentiating agent at the amounts described (in weight percent of the formulation).

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 8.

TABLE 9

| Sample | Methyl Acetate (%) | Flavor (%) | Propylene glycol | Opaque Base | 25% Saccharine | Flavor Intensity | Cooling Intensity |
|---|---|---|---|---|---|---|---|
| 1 | 0 | 1 | 0.5 | 99.32 | 0.8 | 4 | 3 |
| 2 | 0.005 | 1 | 0.495 | 99.32 | 0.8 | 4 | 3.5 |
| 3 | 0.05 | 1 | 0.45 | 99.32 | 0.8 | 4 | 4.5 |
| 4 | 0.5 | 1 | 0 | 99.32 | 0.8 | 3 | 5.5 |

The experiment outlined and reported in Table 9 was repeated. Table 10 below describes seven test formulations. Sample 1 was a control formulation, lacking a potentiating agent. Samples 2-7 contain methyl acetate as the potentiating agent at the amounts described (in weight percent of the formulation).

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 10.

TABLE 10

| Sample | Methyl Acetate (%) | Flavor (%) | Propylene glycol | Opaque Base | 25% Saccharine | Flavor Intensity | Cooling Intensity |
|---|---|---|---|---|---|---|---|
| 1 | 0 | 1 | 0.2 | 98 | 0.8 | 3 | 3 |
| 2 | 0.005 | 1 | 0.195 | 98 | 0.8 | 3.5 | 3.5 |
| 3 | 0.01 | 1 | 0.19 | 98 | 0.8 | 3 | 3.5 |
| 4 | 0.02 | 1 | 0.18 | 98 | 0.8 | 3 | 3.5 |
| 5 | 0.05 | 1 | 0.15 | 98 | 0.8 | 3 | 3.5 |
| 6 | 0.1 | 1 | 0.1 | 98 | 0.8 | 3 | 4 |
| 7 | 0.2 | 1 | 0 | 98 | 0.8 | 3 | 3.5 |

These data suggest that the range of methyl acetate may be between 1 ppm and 10000 ppm. Alternatively between 50 ppm and 5000 ppm, alternatively between 100 ppm and 2000 ppm.

Table 11 below describes four test formulations. Sample 1 was a control formulation, lacking a potentiating agent. Samples 2-4 contain 3-(1-((3,5-dimethylisoxazol-4-yl)methyl)-1H-pyrazol-4-yl)-1-(3-hydroxybenzyl)imidazolidine-2,4-dione as the potentiating agent at the amounts described (in weight percent of the formulation).

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 11.

TABLE 11

| Sample | 3-(1-((3,5-dimethylisoxazol-4-yl)methyl)-1H-pyrazol-4-yl)-1-(3-hydroxybenzyl)imidazolidine-2,4-dione (0.1% solution) (%) | Flavor (%) | Propylene glycol | Opaque Base | 25% Saccharine | Flavor Intensity | Cooling Intensity |
|---|---|---|---|---|---|---|---|
| 1 | 0    | 1 | 20   | 78.2 | 0.8 | 4  | 3  |
| 2 | 0.2  | 1 | 19.8 | 78.2 | 0.8 | 3  | 4  |
| 3 | 2    | 1 | 18   | 78.2 | 0.8 | 3  | 5  |
| 4 | 20   | 1 | 0    | 78.2 | 0.8 | nd | nd |

The experiment outlined and reported in Table 11 was repeated. Table 12 below describes seven test formulations. Sample 1 was a control formulation, lacking a potentiating agent. Samples 2-7 contain 3-(1-((3,5-dimethylisoxazol-4-yl)methyl)-1H-pyrazol-4-yl)-1-(3-hydroxybenzyl)imidazolidine-2,4-dione as the potentiating agent at the amounts described (in weight percent of the formulation).

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 12.

TABLE 12

| Sample | 3-(1-((3,5-dimethylisoxazol-4-yl)methyl)-1H-pyrazol-4-yl)-1-(3-hydroxybenzyl)imidazolidine-2,4-dione (0.1% solution) (%) | Flavor (%) | Propylene glycol | Opaque Base | 25% Saccharine | Flavor Intensity | Cooling Intensity |
|---|---|---|---|---|---|---|---|
| 1 | 0    | 1 | 1    | 97.2 | 0.8 | 3   | 3   |
| 2 | 0.02 | 1 | 0.98 | 97.2 | 0.8 | 3   | 3   |
| 3 | 0.05 | 1 | 0.95 | 97.2 | 0.8 | 3.5 | 3   |
| 4 | 0.1  | 1 | 0.9  | 97.2 | 0.8 | 3.5 | 3.5 |
| 5 | 0.2  | 1 | 0.8  | 97.2 | 0.8 | 3.5 | 4   |
| 6 | 0.5  | 1 | 0.5  | 97.2 | 0.8 | 3.5 | 4   |
| 7 | 1    | 1 | 0    | 97.2 | 0.8 | 3.5 | 4   |

These data suggest that the range of 3-(1-((3,5-dimethylisoxazol-4-yl)methyl)-1H-pyrazol-4-yl)-1-(3-hydroxybenzyl)imidazolidine-2,4-dione in the composition may be between 0.001 ppm and 1000 ppm. Alternatively between 0.02 ppm and 100 ppm, alternatively between 0.2 ppm and 20 ppm.

Example 3

Sensory Evaluation of Compositions According to Some Aspects Presented Herein, Using Two Potentiation Agents Table 13 below describes nine test formulations. Sample 1 was a control formulation, containing 0.05% methyl acetate alone as the potentiating agent. Samples 2-9 contain the mixtures shown in the amounts described (in weight percent of the formulation).

An expert panel of three subjects asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 13.

TABLE 13

| Sample | Methyl Acetate (%) | The Second Potentiation Agent | Flavor | Opaque Base | 25% Saccharine | Flavor Intensity | Cooling Intensity |
|---|---|---|---|---|---|---|---|
| 1 | 0.05 | — | 0.5 | 98.65 | 0.8 | 2 | 2 |
| 2 | 0.05 | 2% of a 0.1% 3-(1-((3,5-dimethylisoxazol-4-yl)methyl)-1H-pyrazol-4-yl)-1-(3-hydroxy-benzyl)imidazolidine-2,4-dione solution | 0.5 | 98.65 | 0.8 | 3 | 4 |
| 3 | 0.05 | 0.1% (+)-methyl(1R)-cis-3-oxo-2-pentyl-1-cyclopentaneacetate | 0.5 | 98.65 | 0.8 | 2 | 2 |
| 4 | 0.05 | 0.2% of a 1% n-(1-propylbutyl)-1,3-benzodioxole-5-carboxamide solution | 0.5 | 98.65 | 0.8 | 2 | 2 |
| 5 | 0.05 | 0.2% of a 10% phloretin solution | 0.5 | 98.65 | 0.8 | 2.5 | 2.5 |
| 6 | 0.05 | 0.05% of chlorogenic acid | 0.5 | 98.65 | 0.8 | 2 | 2 |
| 7 | 0.05 | 0.05% of ferulic acid | 0.5 | 98.65 | 0.8 | 2.5 | 2.5 |
| 8 | 0.05 | 0.1% of a 5% solution of PMF in alcohol | 0.5 | 98.65 | 0.8 | 2 | 2 |
| 9 | 0.05 | 0.1% of a 5% mixture comprising (+-)-4-[(3,3-dimethyl-2-oxiranyl)methoxy]-7H-furo[3,2-g]chromen-7-one, (+-)-4-(2,3-dihydroxy-3-methylbutoxy)-7H-furo[3,2-g]chromen-7-one, 5,7-dimethoxy-2H-chromen-2-one, and (+-)-9-[(3,3-dimethyl-2-oxiranyl)methoxy]-4-methoxy-7H-furo [solution | 0.5 | 98.65 | 0.8 | 2 | 2 |

Solution

Table 14 below describes nine test formulations. Sample 1 was a control formulation, containing 2% of a 0.1% solution of 3-(1-((3,5-dimethylisoxazol-4-yl)methyl)-1H-pyrazol-4-yl)-1-(3-hydroxybenzyl)imidazolidine-2,4-dione alone as the potentiating agent. Samples 2-9 contain the mixtures shown in the amounts described (in weight percent of the formulation).

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 14.

TABLE 14

| Sample | 0.1% Solution of 3-(1-((3,5-dimethylisoxazol-4-yl)methyl)-1H-pyrazol-4-yl)-1-(3-hydroxy-benzyl)imidazolidine-2,4-dione (%) | The Second Potentiation Agent | Flavor | Opaque Base | 25% Saccharine | Flavor Intensity | Cooling Intensity |
|---|---|---|---|---|---|---|---|
| 1 | 2 | — | 0.5 | 96.7 | 0.8 | 2 | 2 |
| 2 | 2 | 0.05% methyl acetate | 0.5 | 96.7 | 0.8 | 2.5 | 3 |

TABLE 14-continued

| Sample | 0.1% Solution of 3-(1-((3,5-dimethylisoxazol-4-yl)methyl)-1H-pyrazol-4-yl)-1-(3-hydroxy-benzyl)imidazolidine-2,4-dione (%) | The Second Potentiation Agent | Flavor | Opaque Base | 25% Saccharine | Flavor Intensity | Cooling Intensity |
|---|---|---|---|---|---|---|---|
| 3 | 2 | 0.1% (+)-methyl(1R)-cis-3-oxo-2-pentyl-1-cyclopentane acetate | 0.5 | 96.7 | 0.8 | 2.5 | 2 |
| 4 | 2 | 0.2% of a 1% n-(1-propylbutyl)-1,3-benzodioxole-5-carboxamide solution | 0.5 | 96.7 | 0.8 | 2.5 | 2.5 |
| 5 | 2 | 0.2% of a 10% phloretin solution | 0.5 | 96.7 | 0.8 | 2.5 | 2 |
| 6 | 2 | 0.05% of chlorogenic acid | 0.5 | 96.7 | 0.8 | 2 | 2 |
| 7 | 2 | 0.05% of ferulic acid | 0.5 | 96.7 | 0.8 | 2 | 2 |
| 8 | 2 | 0.1% of a 5% solution of PMF in alcohol | 0.5 | 96.7 | 0.8 | 2 | 2 |
| 9 | 2 | 0.1% of a 5% mixture comprising (+-)-4-[(3,3-dimethyl-2-oxiranyl)methoxy]-7H-furo[3,2-g]chromen-7-one, (+-)-4-(2,3-dihydroxy-3-methylbutoxy)-7H-furo[3,2-g]chromen-7-one, 5,7-dimethoxy-2H-chromen-2-one, and (+-)-9-[(3,3-dimethyl-2-oxiranyl)methoxy]-4-methoxy-7H-furo[solution | 0.5 | 96.7 | 0.8 | 2 | 2 |

These data suggest that a combination of 3-(1-((3,5-dimethylisoxazol-4-yl)methyl)-1H-pyrazol-4-yl)-1-(3-hydroxybenzyl)imidazolidine-2,4-dione and methyl acetate is most effective at potentiating the flavor and cooling effect perceived by the subject.

Table 15 below describes three test formulations, containing combinations of 3-(1-((3,5-dimethylisoxazol-4-yl)methyl)-1H-pyrazol-4-yl)-1-(3-hydroxybenzyl)imidazolidine-2,4-dione and menthyl acetate at the ratios indicated.

An expert panel of three subjects was asked to evaluate the intensity of the mint flavor and the intensity of the cooling effect of the test formulations. The subjects were asked to apply approximately 1 g of a test sample on to a toothbrush, and rinse the toothbrush under running water for 5 secs to moisten the paste and soften the bristles. The subjects then brushed their teeth with the applied test sample, taking care to minimize any contact with the subjects' gums. The subjects then expectorated the test sample, and rinsed their mouth with water. The subjects then ranked the intensity of the mint flavor and the intensity of the cooling effect of the test formulations. The subjects were asked to wait for 15 min between each test sample. The results are shown in Table 15.

TABLE 15

| Sample | Menthyl Acetate (%) | 0.1% 3-(1-((3,5-dimethylisoxazol-4-yl)methyl)-1H-pyrazol-4-yl)-1-(3-hydroxybenzyl)imidazolidine-2,4-dione Solution (%) | Ratio | Flavor | PG | Opaque base | 25% Saccharine | Flavor Intensity | Cooling Intensity |
|---|---|---|---|---|---|---|---|---|---|
| 1 | 0.05 | 2 | 1:0.04 | 0.5 | 0 | 96.65 | 0.8 | 3.5 | 4 |
| 2 | 0.1 | 0.2 | 1:0.02 | 0.5 | 1.75 | 96.65 | 0.8 | 4 | 4.5 |
| 3 | 0.05 | 0.1 | 1:0.02 | 0.5 | 1.9 | 96.65 | 0.8 | 3 | 3.5 |

These data suggest that the ratio of menthyl acetate to 3-(1-((3,5-dimethylisoxazol-4-yl)methyl)-1H-pyrazol-4-yl)-1-(3-hydroxybenzyl)imidazolidine-2,4-dione in the composition maybe between 1:0.00001 and 1:10. Alternatively between 1:0.0001 and 1:1, alternatively between 1:0.005 and 1:0.1.

Example 4

Sensory Evaluation of Mouthwash Compositions According to Some Aspects Presented Herein The sensory studies outlined in Examples 1 to 3 above will be repeated with oral care compositions comprising mouthwash. Tables 16 to 18 describe some mouthwash compositions that will be tested.

TABLE 16

| Sample | Menthyl Acetate | 0.2% 3-(1-((3,5-dimethylisoxazol-4-yl)methyl)-1H-pyrazol-4-yl)-1-(3-hydroxybenzyl)imidazolidine-2,4-dione | Dosage ppm | Ratio | Flavor | PG | RH40 | 25% Saccharine | Water |
|---|---|---|---|---|---|---|---|---|---|
| 1 | 0.01 | 0 | 100 | — | 0.1 | 1 | 0.4 | 0.08 | 98.41 |
| 2 | 0.01 | 0.01 | 100 + 0.2 | 1:0.002 | 0.1 | 0.99 | 0.4 | 0.08 | 98.41 |
| 3 | 0.01 | 0.1 | 100 + 2 | 1:0.02 | 0.1 | 0.9 | 0.4 | 0.08 | 98.41 |
| 4 | 0.01 | 1 | 100 + 20 | 1:0.2 | 0.1 | 0 | 0.4 | 0.08 | 98.41 |
| 5 | 0 | 0.1 | 2 | — | 0.1 | 0.1 | 0.4 | 0.08 | 99.22 |
| 6 | 0.001 | 0.1 | 10 + 2 | 1:0.2 | 0.1 | 0.099 | 0.4 | 0.08 | 99.22 |
| 7 | 0.01 | 0.1 | 100 + 2 | 1:0.02 | 0.1 | 0.99 | 0.4 | 0.08 | 99.22 |
| 8 | 0.1 | 0.1 | 1000 + 2 | 1:0.002 | 0.1 | 0 | 0.4 | 0.08 | 99.22 |

TABLE 17

| Sample | Menthyl Acetate | Flavor | PG | RH40 | 25% Saccharine | Water |
|---|---|---|---|---|---|---|
| 1 | 0 | 0.1 | 0.1 | 0.4 | 0.08 | 99.32 |
| 2 | 0.005 | 0.1 | 0.099 | 0.4 | 0.08 | 99.32 |
| 3 | 0.01 | 0.1 | 0.09 | 0.4 | 0.08 | 99.32 |
| 4 | 0.02 | 0.1 | 0.08 | 0.4 | 0.08 | 99.32 |
| 5 | 0.1 | 0.1 | 0 | 0.4 | 0.08 | 99.32 |

TABLE 18

| Sample | 0.2% 3-(1-((3,5-dimethylisoxazol-4-yl)methyl)-1H-pyrazol-4-yl)-1-(3-hydroxybenzyl)imidazolidine-2,4-dione | Flavor | PG | RH40 | 25% Saccharine | Water |
|---|---|---|---|---|---|---|
| 1 | 0 | 0.1 | 1 | 0.4 | 0.08 | 99.42 |
| 2 | 0.01 | 0.1 | 0.99 | 0.4 | 0.08 | 99.42 |
| 3 | 0.1 | 0.1 | 0.9 | 0.4 | 0.08 | 99.42 |
| 4 | 0.2 | 0.1 | 0.08 | 0.4 | 0.08 | 99.42 |
| 5 | 1 | 0.1 | 0 | 0.4 | 0.08 | 99.42 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A composition, comprising:
a. at least one cooling compound;
b. methyl acetate at a concentration ranging from 1 ppm to 100 ppm; and
c. a water-soluble artificial sweetener, wherein the at least one cooling compound comprises menthol, mint oil, peppermint oil, or a combination thereof.

2. The composition of claim 1, further comprising an orally acceptable carrier.

3. The composition of claim 1, wherein the water-soluble artificial sweetener is saccharin or a salt thereof.

4. The composition of claim 1, further comprising a potentiating agent selected from the group consisting of (+)-methyl(1R)-cis-3-oxo-2-pentyl-1-cyclopentaneacetate, n-(1-propylbutyl)-1,3-benzodioxole-5-carboxamide, phloretin, ferulic acid, a cyclohexanecarboxylic acid, a mixture comprising (+)-4-[(3,3-dimethyl-2-oxiranyl)methoxy]-7H-furo[3,2-g]chromen-7-one, (+)-4-(2,3-dihydroxy-3-methylbutoxy)-7H-furo[3,2-g]chromen-7-one, 5,7-dimethoxy-2H-chromen-2-one, (+)-9-[(3,3-dimethyl-2-oxiranyl)methoxy]-4-methoxy-7H-furo[3,2-g]chromen-7-one, a polymethoxy flavonoid, 3-(1-((3,5-dimethylisoxazol-4-yl)methyl)-1H-pyrazol-4-yl)-1-(3-hydroxybenzyl)imidazolidine-2,4-dione, and combinations thereof.

5. The composition of claim 4, wherein the potentiating agent is 3-(1-((3,5-dimethylisoxazol-4-yl)methyl)-1H-pyrazol-4-yl)-1-(3-hydroxybenzyl)imidazolidine-2,4-dione.

6. The composition of claim 4, wherein the ratio of the methyl acetate to the potentiating agent is from 1:0.0001 to 1:1.

7. The composition of claim 4, wherein the ratio of the methyl acetate to the potentiating agent is from 1:0.0005 to 1:0.1.

8. The composition of claim 4, wherein the methyl acetate and the potentiating agent are present in a combined amount sufficient to increase an intensity of a flavor of the at least one cooling compound and increase an intensity of a cooling sensation of the at least one cooling compound when a subject is contacted with the composition, and wherein the amount sufficient is from 100 ppm to 10,000 ppm.

* * * * *